US009987396B1

(12) United States Patent
Wustenberg et al.

(10) Patent No.: US 9,987,396 B1
(45) Date of Patent: *Jun. 5, 2018

(54) REDUCTION OF IMPLANT INFECTION VIA TUNABLE STIMULATION OF LOCALIZED ADAPTIVE IMMUNE RESPONSE

(71) Applicant: Biospheres, Inc., Minneapolis, MN (US)

(72) Inventors: William Wustenberg, Farmington, MN (US); Michael D Finch, Apple Valley, MN (US); Cyrus B. Munshi, Blaine, MN (US)

(73) Assignee: BIOSPHERES, INC., Minneapolis, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/712,859

(22) Filed: Sep. 22, 2017

Related U.S. Application Data

(63) Continuation of application No. 14/347,551, filed as application No. PCT/US2012/057194 on Sep. 26, 2012, now Pat. No. 9,782,520.
(Continued)

(51) Int. Cl.
*A61L 31/10* (2006.01)
*A61K 9/14* (2006.01)
(Continued)

(52) U.S. Cl.
CPC .............. *A61L 31/10* (2013.01); *A61K 9/14* (2013.01); *A61K 9/1611* (2013.01); *A61K 9/1635* (2013.01); *A61K 9/1647* (2013.01); *A61K 9/5115* (2013.01); *A61K 9/5138* (2013.01); *A61K 9/5153* (2013.01);
(Continued)

(58) Field of Classification Search
CPC .......... A61L 31/10; A61L 15/46; A61L 29/16; A61L 17/005; A61L 31/16; A61L 27/54; A61L 31/048; A61L 2400/12; A61L 2300/404; A61L 2300/606; A61K 9/14; A61K 45/06; A61K 9/5138; A61K 31/745; A61K 9/1647; A61K 9/5115; A61K 9/1611; A61K 9/5153; A61K 9/1635
See application file for complete search history.

(56) References Cited

U.S. PATENT DOCUMENTS

| 4,732,763 A | 3/1988 | Beck et al. |
| 2007/0282247 A1 | 12/2007 | Desai et al. |

(Continued)

OTHER PUBLICATIONS

"U.S. Appl. No. 14/347,551, Advisory Action dated Dec. 28, 2016", 5 pgs.
(Continued)

*Primary Examiner* — Trevor Love
(74) *Attorney, Agent, or Firm* — Schwegman Lundberg & Woessner, P.A.

(57) ABSTRACT

Compositions, implantation devices and methods for stimulating an immune response to infection are discussed. In some examples, the compositions, implantation devices or methods of regulating the amplification of an adaptive immune response to infection involves use of one or more particles locally at a surgical or implant site to control bacterial infections without detrimental systemic side-effects. In some examples, the particles can be coated or layered onto the surface of an implantable device or material. In other examples, the particles can be injected into the site of implantation.

11 Claims, 9 Drawing Sheets

Related U.S. Application Data

(60) Provisional application No. 61/539,282, filed on Sep. 26, 2011.

(51) Int. Cl.

| | | |
|---|---|---|
| *A61K 45/06* | (2006.01) | |
| *A61K 9/51* | (2006.01) | |
| *A61K 31/745* | (2006.01) | |
| *A61L 15/46* | (2006.01) | |
| *A61K 9/16* | (2006.01) | |
| *A61L 29/16* | (2006.01) | |
| *A61L 17/00* | (2006.01) | |
| *A61L 31/16* | (2006.01) | |
| *A61L 27/54* | (2006.01) | |
| *A61L 31/04* | (2006.01) | |

(52) U.S. Cl.
CPC ............ *A61K 31/745* (2013.01); *A61K 45/06* (2013.01); *A61L 15/46* (2013.01); *A61L 17/005* (2013.01); *A61L 27/54* (2013.01); *A61L 29/16* (2013.01); *A61L 31/048* (2013.01); *A61L 31/16* (2013.01); *A61L 2300/404* (2013.01); *A61L 2300/606* (2013.01); *A61L 2400/12* (2013.01)

(56) References Cited

U.S. PATENT DOCUMENTS

| | | | |
|---|---|---|---|
| 2008/0124400 | A1 | 5/2008 | Liggins et al. |
| 2010/0003300 | A1 | 1/2010 | Markland et al. |
| 2010/0104652 | A1 | 4/2010 | Biris et al. |
| 2010/0268335 | A1 | 10/2010 | Yang et al. |
| 2010/0317617 | A1 | 12/2010 | Mousa et al. |
| 2015/0125505 | A1 | 5/2015 | Wustenberg et al. |

OTHER PUBLICATIONS

"U.S. Appl. No. 14/347,551, Applicant Interview Summary filed Jan. 4, 2017 to Examiner Interview Summary dated Dec. 19, 2016", 1 pg.
"U.S. Appl. No. 14/347,551, Examiner Interview dated Dec. 9, 2016", 3 pgs.
"U.S. Appl. No. 14/347,551, Examiner Interview Summary dated Apr. 14, 2015", 3 pgs.
"U.S. Appl. No. 14/347,551, Examiner Interview Summary dated Nov. 20, 2015", 3 pgs.
"U.S. Appl. No. 14/347,551, Final Office Action dated Apr. 6, 2016", 13 pgs.
"U.S. Appl. No. 14/347,551, Final Office Action dated Nov. 9, 2016", 10 pgs.
"U.S. Appl. No. 14/347,551, Non Final Office Action dated Jun. 16, 2016", 13 pgs.
"U.S. Appl. No. 14/347,551, Non Final Office Action dated Jun. 25, 2015", 13 pgs.
"U.S. Appl. No. 14/347,551, Notice of Allowance dated Jun. 1, 2017", 11 pgs.
"U.S. Appl. No. 14/347,551, Preliminary Amendment filed Mar. 26, 2014", 13 pgs.
"U.S. Appl. No. 14/347,551, Response filed May 26, 2015 to Restriction Requirement dated Mar. 23, 2015", 2 pgs.
"U.S. Appl. No. 14/347,551, Response filed Jun. 8, 2016 to Final Office Action dated Apr. 6, 2016", 10 pgs.
"U.S. Appl. No. 14/347,551, Response filed Dec. 13, 2016 to Final Office Action dated Nov. 9, 2016", 9 pgs.
"U.S. Appl. No. 14/347,551, Response filed Dec. 21, 2015 to Non Final Office Action dated Jun. 25, 2015", 11 pgs.
"U.S. Appl. No. 14/347,551, Restriction Requirement dated Mar. 23, 2015", 10 pgs.
"U.S. Appl. No. 14/347,551, Examiner Interview Summary dated Jul. 25, 2016", 3 pgs.
"U.S. Appl. No. 14/347,551, Response filed Aug. 3, 2016 to Non-Final Office Action dated Jun. 16, 2016", 10 pgs.
"International Application Serial No. PCT/US2012/057194, International Preliminary Report on Patentability dated Apr. 10, 2014", 14 pgs.
"International Application Serial No. PCT/US2012/057194, International Search Report dated May 13, 2013", 7 pgs.
"International Application Serial No. PCT/US2012/057194, Written Opinion dated May 13, 2013", 13 pgs.
Lara, Humberto H, et al., "Bactericidal effect of silver nanoparticles against multidrug-resistant bacteria", World Journal of Microbiology and Biotechnology, Kluwer Academic Publishers, vol. 26, No. 4, (Oct. 22, 2009), 615-621.
Schug, Pab, et al., "Does the additional application of a polylactide film (SurgiWrap) to a lightweight mesh (TiMesh) reduce adhesions after laparoscopic intraperitoneal implantation procedures?", Experimental results obtained with the laparoscopic porcine model, Surg Eng, 22, (2008), 2433-2439.

FIG. 7A

| TIME (hr) | Gluc | | | | Gln | | | | Lac | | | |
|---|---|---|---|---|---|---|---|---|---|---|---|---|
| | PARTICLE FREE | 0.1μm | 0.5μm | 1.0μm | PARTICLE FREE | 0.1μm | 0.5μm | 1.0μm | PARTICLE FREE | 0.1μm | 0.5μm | 1.0μm |
| 0 | 5.50 | 5.50 | 5.50 | 5.50 | 4.00 | 4.00 | 4.00 | 4.00 | 0 | 0 | 0 | 0 |
| 24 | 3.87 | 3.65 | 3.87 | 3.55 | 3.76 | 3.91 | 3.67 | 3.55 | 2.41 | 2.32 | 1.98 | 2.06 |
| 48 | 1.86 | 1.32 | 1.88 | 2.01 | 2.10 | 2.25 | 2.33 | 2.41 | 3.36 | 3.57 | 3.22 | 3.10 |
| 72 | 0.37 | 0.53 | 0.67 | 0.59 | 1.10 | 1.43 | 1.62 | 1.49 | 4.37 | 4.87 | 4.38 | 4.21 |

FIG. 7B

| TIME (hr) | Gluc | | | | Gln | | | | Lac | | | |
|---|---|---|---|---|---|---|---|---|---|---|---|---|
| | PARTICLE FREE | 0.1μm | 0.5μm | 1.0μm | PARTICLE FREE | 0.1μm | 0.5μm | 1.0μm | PARTICLE FREE | 0.1μm | 0.5μm | 1.0μm |
| 0 | 5.50 | 5.50 | 5.50 | 5.50 | 4.00 | 4.00 | 4.00 | 4.00 | 0 | 0 | 0 | 0 |
| 24 | 3.87 | 5.01 | 4.98 | 4.77 | 3.76 | 3.76 | 3.81 | 3.54 | 2.41 | 0.87 | 0.91 | 1.01 |
| 48 | 1.86 | 4.56 | 4.62 | 4.57 | 2.10 | 3.32 | 3.44 | 3.01 | 3.36 | 1.56 | 1.67 | 1.71 |
| 72 | 0.37 | 2.99 | 3.10 | 2.78 | 1.10 | 2.91 | 2.98 | 2.67 | 4.37 | 2.89 | 2.77 | 2.69 |

# REDUCTION OF IMPLANT INFECTION VIA TUNABLE STIMULATION OF LOCALIZED ADAPTIVE IMMUNE RESPONSE

This application is a divisional of U.S. patent application Ser. No. 14/347,551, filed Mar. 26, 2014, which is a U.S. National Stage Application filed under 35 U.S.C. § 371 from International Application Serial No. PCT/US2012/057194, filed Sep. 26, 2012, which claims benefit of the priority filing date of U.S. Provisional Patent Application Ser. No. 61/539,282, filed Sep. 26, 2011, the contents of which are specifically incorporated herein in their entirety.

BACKGROUND

Implanted medical devices or biomaterials can present microenvironments that are conducive to bacterial colonization or infection. Such infections can require repetitive hospital visits or can even require removal or replacement of the implanted device or material. For example, approximately 1 million inguinal and 20,000 ventral herniorrhaphies are performed yearly in the United States. It is estimated that approximately 3 to 8 percent of patients who undergo such surgery develop post-operative infections. These types of infections can cause complications that require longer post-surgery care and escalate health care costs. It has been estimated that surgical site infections have increased hospital stays by approximately 7 days with costs increasing from $3,000 to $30,000. Overall surgical implant infections costs have been credited with increasing direct medical costs by more than $3 billion annually in the US. In addition to the financial burden caused by repetitive implant surgery and longer inpatient hospital stays, infections can be fatal or near fatal to a significant portion of patients.

At least some degree of bacterial entry into a surgical site is nearly unavoidable at the time of surgery. Bacteria can be introduced in surgeries that include the implantation of medical devices and materials as well as surgeries that do not. However, the presence of an implant can complicate the clearance of bacteria from the surgical site. Bacteria introduced at the time of implantation can 30 contact the implant, bind to and colonize the implant surface. If bacterial colonization occurs on the surface of the implant, traditional means of treatment including the use of systemic antibiotics, are largely unsuccessful in treating the infection. Because of the difficulty of clearing bacteria that have populated the implant surface, it is common for surgeons to completely remove the implant, place patients on long term systemic antibiotics to clear the infection, and re-implant the medical device.

Currently available procedures for treating infections typically involve administration of antibiotics. Others such as Gristina et al. (U.S. Pat. No. 5,292,513) disclose methods for nonspecific cellular immune stimulation. Ziegler et al. (U.S. Pat. No. 7,906,132) disclose anti-infectious, biocompatible titanium coating for implants, and methods for the production thereof. O'Hagan et al. U.S. Pat. No. 7,597,908 discloses use of micro-particles with adsorbed antigen to stimulate immune responses towards the specific antigen at a systemic level.

SUMMARY

The present inventors have recognized, among other things, that a reduction or elimination of implant-related bacterial infections can be achieved by use of micro- and nano-sized particles that promote a regulated and localized immune response to bacteria.

One aspect of the invention is a composition that includes particles having a diameter of about 1.0 nm to about 100 µm. Such a composition can be administered, for example, to a localized site in an animal for reducing microbial infection at the site in the animal. The composition can also be used to coat, or be administered with, an implant or implantation device.

Another aspect of the invention is an implant or implantation device that includes one or more surfaces configured for implantation into an animal, and a coating on the one or more surfaces, where the coating includes a composition having particles with a diameter of about 1.0 nm to about 100 µm.

Another aspect of the invention is a method of reducing a microbial infection at a site in an animal in need thereof that includes locally administering to the site an effective amount of a composition that includes particles having a diameter of about 1.0 nm to about 100 µm, to thereby reduce microbial infection at the site in the animal.

In some embodiments, the compositions, the coatings or the particles are adapted or configured to biodegrade after activating macrophages at the site without substantial activation of neutrophils.

Such compositions, methods, implants or implantation devices can reduce bacterial titer at the site of administration by at least 30%, or at least 40%, or at least 50%, or at least 60%, or at least 70%, or at least 80%, or at least 90%, or at least 95%.

A variety of materials can be used in the particles. For example, the particles in the composition can include any of the materials described herein such as metal, silica, alumina, titania, glass, ceramic, polystyrene, polymethylmethacrylate, polystyrene, melamine, polylactide, magnetic material, radioactive material, or a combination thereof.

In some embodiments, the particles are adapted or configured for adhesion to bacteria. For example, a portion of the particles in a composition or coating can be adapted or configured for adhesion to bacteria. In some embodiments, at least about 50%, or at least about 60%, at least about 70%, or at least about 80%, at least about 90%, or at least about 95% of the particles in a composition or coating can be adapted or configured for adhesion to bacteria.

Particles in the compositions or coatings can have a distribution of sizes. For example, a portion of the particles in a composition or coating can be of a selected diameter size range. In some embodiments, at least about 50%, or at least about 60%, at least about 700%, or at least about 80%, at least about 900%, or at least about 95% of the particles in a composition or coating can have a diameter falling in the range of about 100 nm to about 0.5 µm.

Particles in the compositions or coatings can also have a variety of shapes. For example, a portion of the particles in a composition or coating can have a shape that is substantially smooth, spherical, square, rectangular, planar, cuboidal, or a combination thereof. In some embodiments, at least about 50%, or at least about 60%, at least about 70%, or at least about 80%, at least about 90%, or at least about 95% of the particles can have a shape that is substantially smooth, spherical, square, rectangular, planar, cuboidal, or a combination thereof.

Particles in the compositions or coatings can also have a surface that is rough. For example, a portion of the particles in a composition or coating can have an average surface roughness greater than 0.1 or 0.2 microns. In some embodiments, at least about 50%, or at least about 60%, at least about 70%, or at least about 80%, at least about 90%, or at least about 95% of the particles can have an average surface roughness greater than 0.05 microns, 0.1 microns, 0.2 microns, 0.3 microns, or 0.4 microns.

The composition can coat or be administered with an implant or implantation device. Such an implant or implantation device can include a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or any other implantable medical device.

The compositions can coat or be administered with an implant or implantation device into a variety of sites within an animal. For example, the implant or implantation device can be configured for implantation into a bone, a blood vessel, a hernia, a breast, a bladder, an anus, a vagina, or a penis. Alternatively, the composition can be administered in sites that contain or do not contain an implant or implantation device. For example, the composition can be administered in sites such as a bone, a blood vessel, a hernia, a breast, a bladder, an anus, a vagina, or a penis.

Implants or implantation devices can be coated with one or more layers of a particle composition. In some embodiments, one or more layers are configured to peel-off over a time period of about 1 hour to about 1 week after the implant or implantation device is administered.

The compositions and coatings can also include a variety of other agents. For example, the compositions and coatings can also include an anti-bacterial agent, an anti-fungal agent, an anti-inflammatory agent, a chemotherapeutic agent, a cytokine, a chemokine, an antibody, a peptide, a recombinant DNA, or a combination thereof. Other agents that can be included in the compositions and coatings are further described herein.

BRIEF DESCRIPTION OF THE FIGURES

FIGS. 1A & 1B show images of control cells. FIG. 1C shows images of cells incubated with 10 µm particles, for 24 hours, at a density of $2.5\times10^5$ particles/cm$^2$. FIG. 1D shows images of cells incubated with 10 µm particles, for 24 hours, at a density of $5.0\times10^5$ particles/cm$^2$. FIG. 1E shows images of cells incubated with 10 µm particles, for 24 hours, at a density of $7.5\times10^5$ particles/cm$^2$. FIG. 1F shows images of cells incubated with 10 µm particles, for 24 hours, at a density of $10.0\times10^5$ particles/cm$^2$.

In FIGS. 5A-C, the cells were exposed to particles for twelve hours. In FIG. 5A the particle size was 0.1 µm, 0.5 µm in FIG. 5B, and 1.0 µm in FIG. 5C. In FIG. 5D, the cells were continuously incubated with particles, the sizes being 0.1 µm, 0.5 µm, and 1.0 µm, as shown.

In FIGS. 6A-C, the cells were exposed to particles for twelve hours. In FIG. 6A the particle size was 0.1 µm, 0.5 µm in FIG. 6B, and 1.0 µm in FIG. 6C. In FIG. 6D, the cells were continuously incubated with particles, the sizes being 0.1 µm, 0.5 µm, and 1.0 µm, as shown.

FIGS. 7A-7B shows the impact of particles on cell metabolism. In FIG. 7A, cells were incubated with particles for 15 hours. In FIG. 7B, cells were incubated with particles for 72 hours. In both, results are shown for the metabolic bioanalysis of glucose, glutamine and lactose, at 0, 24, 48, and 72 hours.

FIG. 8A shows the images of control rat quadriceps slices, taken from animals that have been injected with 50 µl of PBS. FIGS. 8B-D show rat quadriceps slices taken from animals that had been injected with 50 µl of 1.0 µm particles suspended in PBS at a concentration of 25 mg/ml.

DETAILED DESCRIPTION

Figure 1E:
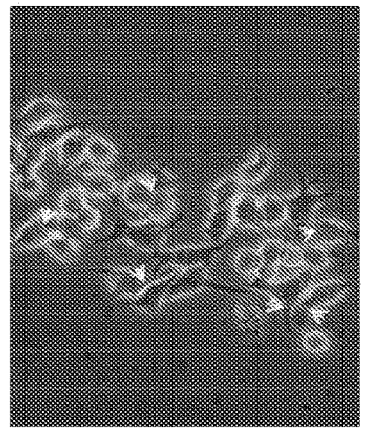
FIG. 1A-1F shows microscopic images of RAW 264.7 cells, some of which were incubated with particles at different densities.
Figure 1F:
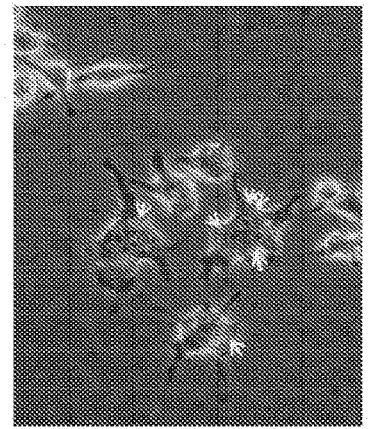
Figure 1C:
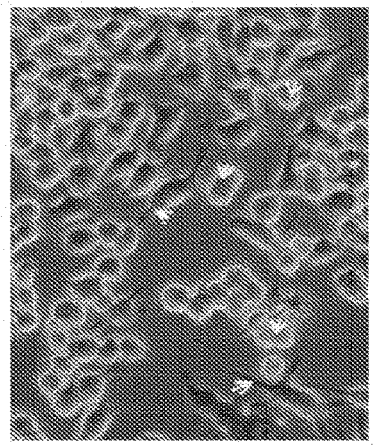
Figure 1D:
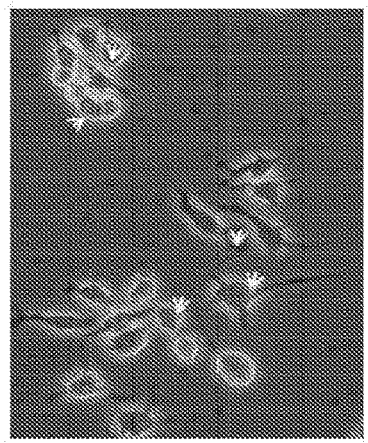
Figure 1A:
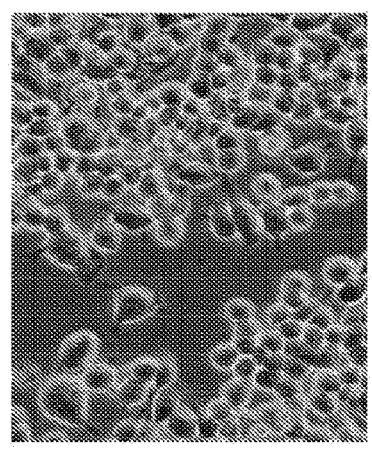
Figure 1B:
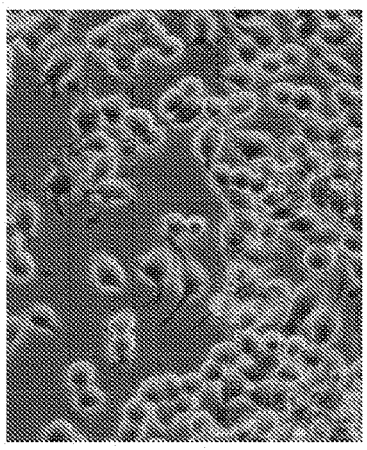

Although methods for battling infections are widely used, substantial numbers of implant-related bacterial infections persist. Existing technologies fail to address the underlying impairment of the local cell mediated immune response. The inventors have noted that clearance of viable bacteria from an infected surgical implant is most effective when a viable immune response occurs. Such clearance is important for defeating infection even when antimicrobials are also administered. Accordingly, patients, including immune-compromised individuals, remain exceedingly difficult to treat successfully.

Applicants have solved this problem by providing methods, implants and compositions that induce a particle-mediated immune response effective against localized bacterial infections. Such methods, implants and compositions can also reduce or minimize deleterious side effects of implantation procedures. Moreover, such a particle-mediated immune response can be regulated and is tunable through the practice of the methods described herein. Thus, the inventors have developed compositions, implants and methods to up-regulate a cell mediated immune response at a site of infection or at a surgical implant site in a subject that reduces bacterial adherence to an implant surface and by improving bacterial phagocytosis and clearance from sites of infection without impairing other aspects of a normal healing response.

Definitions

As described herein, a particle-mediated immune response refers to a subject's immune response that is initiated, amplified, minimized, or otherwise altered by the presence of a micro-particle or nano-particle.

As described herein, an innate immune response refers to the immune response of subjects to innately prevent, eradicate or reduce pathogenic infections. Such an innate immune response is mediated by granulocytes, leukocytes, monocytes, macrophages, mononuclear phagocytes, neutrophils, and the like. Such cells, particularly neutrophils and macrophages, are effective during innate antibacterial defense because they provide a diverse array of highly specialized cellular functions, including phagocytic uptake of the bacterium, generation of phagolysosomes, production of reactive oxygen species, activation of inducible nitric oxide synthase (iNOS), and release of antimicrobial peptides (e.g. cathelicidins, defensins) and granule proteases (e.g. elastase, cathepsin). However, some of these cells and functions are more effective at reducing localized infections and promoting healing than others. For example, neutrophils can emigrate to a site or injury or infection, and release cytotoxic compounds, including oxidants, proteases and cytokines. Although neutrophils are important in fighting infection, they can promote tissue darriage. For example, neutrophils can cause significant damage at healthy tissue sites by releasing toxic substances at a vascular wall or uninjured tissue.

As described herein, the term macrophage generally means a phagocytic cell 10 that plays a role in innate as well as the adaptive immune response. Macrophages phagocytose debris, foreign substances, and pathogens, and stimulate other cells involved in an immune response. The term macrophage, as used herein, covers not only neutrophils, but also neutrophil-like cells.

As described herein, the term neutrophil generally means a white blood cell that makes up part of the innate immune system. Neutrophils typically have segmented nuclei, containing about 2-5 lobes. Neutrophils frequently migrate to the site of an injury within minutes following trauma. The term neutrophils, as used herein, covers not only neutrophils, but also neutrophil-like cells.

As described herein, an activated macrophage is generally a macrophage that undergoes a functional, biochemical or morphological change, including but not limited to membrane ruffling, peroxide elaboration, increased expression of antigens, increased secretion of plasminogen, or a combination of any of these.

As described herein, an effective amount generally means an amount which provides the desired local or systemic effect, e.g., effective to ameliorate undesirable effects of infection or inflammation, including modulation of activation of macrophages, etc. For example, an effective amount is an amount sufficient to effectuate a beneficial or desired clinical result. An effective amount can be provided all at once in a single administration or in fractional amounts that provide the effective amount in several administrations. The precise determination of what would be considered an effective amount may be based on factors individual to each subject, including their size, age, injury, disease or infection being treated, and amount of time since the injury occurred or disease or infection began. One skilled in the art will be able to determine the effective amount for a given subject based on these considerations which are routine in the art.

As described herein, a particle refers to a general designation for a material that can create a good microclimate for a biologically active substance incorporated therein such that the material has a suitable bioactivity. As used herein, the term particle is used to designate a particle with an average diameter within the range of about 1 µm to about 100 µm. As used herein, the term nanoparticle is used to designate a particle with an average diameter within the range of about 50 nm to 10 about 1000 nm.

The terms treating, treatment and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease, i.e., infection. As such, the term treatment as used herein covers any treatment of a disease in a mammal, particularly a human, and includes: preventing the disease from occurring in a subject which may be predisposed to the disease but has not yet been diagnosed with the disease; inhibiting the disease, such as by arresting its development; or relieving the disease, such as by mitigating or ameliorating the disease and/or its symptoms or conditions. As used herein, treating or treatment of a disease involves treating a patient's infection.

Microbial pathogens include a large and diverse group of organisms capable of infecting animals and plants, such as bacteria, protozoa, fungi, nematodes, and viruses. Initiation of an infection occurs when the infecting organism is pathogenic, and the host is susceptible to pathogenic invasion. After establishing contact with susceptible cells or tissues of the host, the pathogen acquires nutrients from its host, facilitating its own survival. During the infection process the pathogen activates a cascade of molecular, biochemical, and physiological processes, the result of which is the release of substances detrimental to the host and the development of disease (See, e.g., Scientific American Medicine, W.H. Freeman and Co., San Francisco, 1995; Agrios, G. N., Plant Pathology, Academic Press, 1988 Finlay B B, Falkow S. Common themes in microbial pathogenicity revisited. Microbiol Mol Biol Rev. 1997 June; 61(2): 136-69.). The pathogenic effects of microbes are produced in a variety of ways. The term pathogen includes both obligate and opportunistic organisms including bacteria, protozoa, fungi, nematodes, viruses, and other factors which may cause infective and/or inflammatory responses. In one embodiment, the invention is directed to treating infectivity or virulence of pathogens. Accordingly, in one embodiment, the instant invention pertains to methods of reducing the infectivity or virulence of a pathogen.

As used herein, the term biodegradable means that the composition, after administration, is dissolved, chemically degraded, enzymatically degraded or metabolized in a physiological environment (e.g., the body of an animal) to form endogenic substances. For example, polymers that make up a biodegradable particle or are otherwise present in a composition can be dissolved or metabolized to yield glucose. The biodegradability can be examined through injection or other administration of microparticles, for example subcutaneously or intramuscularly, and histological examination of the tissue as a function of time. The term biodegradable polymer refers to a material, which is degraded in the biological environment of the cell or subject in which it is found. In one embodiment, the biodegradable polymer can be included in the composition. The included biodegradable polymer can undergo degradation, wherein acidic products, or in another embodiment, basic products are released. The biodegradability can be determined or examined through incubation with a suitable enzyme, for example alpha-amylase, in vitro. In one embodiment, biodegradation involves the degradation of the polymer into its component subunits, via, for example, digestion, by a biochemical process. In one embodiment, biodegradation may involve cleavage of bonds (whether covalent or otherwise) in the polymer backbone. In one embodiment, biodegradation may involve cleavage of a bond (whether covalent or otherwise) internal to a side-chain or one that connects a side chain to the polymer backbone.

The term coating as used herein can refer to the physical attachment of a particle to an implantable device, or in another embodiment, the association of a coating with an implantable device. The term coating can also refer to a type of composition that facilitates attachment or association of a particle to an implantable device. Such a coating can include particles. Thus, the application of a composition can be in the form of a coating. The coating can be in a pattern, or on specific regions of an implantable device to suit a particular purpose. The application of a coating can be random. The coating can include a film, containing a particle. The term coating applies not only to a surface coating of an implantable device, but is to be understood as encompassing embedding and/or impregnating the implantable device, in whole, or in some embodiments, in part, with the particles described herein. In some embodiments, the embedding and/or impregnating the composition may be according to a desired pattern and/or design, to suit a particular purpose or application. In some embodiments, multiple coatings may be impregnated or embedded in the implantable device. In some embodiments, the coating is applied to the surface of an implantable device. The coating may be applied according to a particular pattern or design, which may be the same, or in another embodiment, different than the patterning of a first coating. For example, the coating can vary in terms of the percent by weight, or in some embodiments, in terms of the composition of the coating in different parts of an implantable device. In an embodiment, bacteria can adhere to the coating or to particles in the coating.

The coating can include a single layer, or multiple layers. The coating can be 1, 2, 3, 4, 5, 6, 7, 8, 9, 10, 15, 20, 25, 30, 35, 40, 45, 50 or more layers. A layer can be of any thickness, such as 0.05-2.0 Angstroms. The coating can range from 0.05 Angstroms to 3 millimeters or more. When the coating can include multiple layers, where one or more layers can be configured to peel-off after administration. The term peel-off indicates that the coating can biodegrade, as discussed above, in a uniform or non-uniform manner. In an embodiment, the one or more layers can peel-off from a time of about 1 hour to about 1 week. The one or more layer can peel-off over a time period of about more than a month, 3 weeks, 2 weeks, 1 week, 144 hours, 120 hours, 96 hours, 72 hours, 48 hours, 24 hours, 12 hours, 6 hours, 5 hours, 4 hours, 3 hours, 2 hours, 1 hour, less than 1 hour, or immediately upon administration. In another embodiment, the coating can biodegrade in a uniform manner. The biodegradation can permit a particle to be released from a time period of about 1 hour to about 1 week. A particle can be released over a time period of about more than a month, 3 weeks, 2 weeks, 1 week, 144 hours, 120 hours, 96 hours, 72 hours, 48 hours, 24 hours, 12 hours, 6 hours, 5 hours, 4 hours, 3 hours, 2 hours, 1 hour, less than 1 hour, or immediately upon administration.

Particle Compositions and Implants

One aspect of the invention is a composition comprising particles having a diameter of about 1.0 nm to about 100 µm, to thereby reduce microbial infection at the site in the animal. The particles in the composition can inhibit bacteria from adhering to or colonizing the site. In some embodiments, the composition or the particles in the composition are configured to biodegrade after activating macrophages without substantial activation of neutrophils.

The compositions can be administered at localized sites in an animal, for example, at sites that are infected or may become infected. The compositions can also be administered at sites of implants or implantation devices in an animal, before, during or after the implant or implantation device is placed within the animal.

Implants and/or implantation devices can also be coated with such a particle composition and such implants and/or implantation devices can then be administered When coating implants and implantation devices with such particle compositions, the composition can be applied to, embedded within, or impregnated into the implant or implantation device. In an embodiment, the applying, embedding or impregnating of the composition may be to a particular surface of an implantable device to suit a particular purpose or application. The applying, embedding or impregnating can be in a particular pattern or design, to suit a particular purpose or application. In some embodiments, the applying, embedding or impregnating of the composition may be to two or more surfaces of the implantable device. The particular pattern or design can vary as a function of the surface of the implantable device to which the composition is being applied, embedded or impregnated within.

By way of illustration, the composition can be a part of, in the form of, or applied to an implantable medical device, such as a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or any other implantable medical device. In one embodiment, the catheter is a pulmonary artery, pericardial, pleural, urinary or 10 intra-abdominal catheter. The implantable medical device can be configured for implantation into bone, a blood vessel, a hernia, breast, bladder, anus, vagina, penis, or any other site.

In one embodiment, the particles can be administered without being associated with an additional material, implant or implantable device. In another embodiment, the particles can be administered in a composition.

In an embodiment, the particles can be administered by injection.

An injectable formulation having particles can include one or more additional therapeutic agents including pharmacologically active substances. Therapeutic agents which may be delivered include, for example, proteins, peptides, nucleic acids and small organic molecules, for example local anesthetics (such as cocaine, procaine and lidocaine), hypnotics or sedatives (such as barbiturates, benzodiazepines and chloral derivatives), psychiatric agents (such as phenothiazines, tricyclic antidepressants and monoamine oxidase inhibitors), antiepilepsy compounds (such as hydantoins), L-dopa, opium-based alkaloids, analgesics, anti-inflammatories, allopurinol, cancer chemotherapeutic agents, anticholinesterases, sympathomimetics (such as epinephrine, salbutamol and ephedrine), antimuscarinics (such as atropine), u-adrenergic blocking agents (such as phentolamine), j3-adrenergic blocking agents (such as propranolol), ganglionic stimulating and blocking agents (such as nicotine), neuromuscular blocking agents, 30 autacoids (such as anti-histamines and 5-HT antagonists), prostaglandins, plasma kinins (such as bradykinin), cardiovascular drugs (such as digitalis), antiarrhythmic drugs, antihypertensives, vasodilators (such as amyl nitrate and nitroglycerin) diuretics, oxytocin, antibiotics, anthelminthics, fungicides, antiviral compounds (such as acyclovir), antitrypanosomals, anticoagulants, sex hormones (for example for HRT or contraception), insulin, alprostidil, blood-clotting factors, calcitonin, growth hormones, vaccines, constructs for gene therapy, steroids or any combination thereof.

A composition can include at least a second compound, such as an antiviral, an anti-helminth, an anti-inflammatory, an antihistamine, an immunomodulatory, an anticoagulant, a surfactant, a bronchodilator, an antibody, a beta-adrenergic receptor inhibitor, a calcium channel blocker, an ace inhibitor, a growth factor, a hormone, a DNA, an siRNA, a vector or any combination thereof.

A composition can include an anti-bacterial agent, an anti-fungal agent, an anti-inflammatory agent, an anti-cancer agent, or a combination thereof. The antibacterial agent, an anti-fungal agent, an anti-inflammatory agent, an anti-cancer agent, or a combination can be released over a time period of about more than a month, 3 weeks, 2 weeks, 1 week, 144 hours, 120 hours, 96 hours, 72 hours, 48 hours, 24 hours, 12 hours, 6 hours, 5 hours, 4 hours, 3 hours, 2 hours, 1 hour, less than 1 hour, or immediately upon administration. The anti-bacterial agent, an antifungal agent, an anti-inflammatory agent, an anti-cancer agent or combination thereof can be in the concentration range of about 0.01 mg per cm2 to about 30 mg per $cm^2$ or greater.

When the composition can include an antibacterial agent, the antibacterial agent can, for example, be selected from the group consisting of β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, cefriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol or any combination thereof.

When the composition includes an antifungal agent, the agent can, for example, be selected from the group consisting of amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid, undecylenate salts (calcium undecylenate, copper undecylenate, zinc undecylenate) or any combination thereof.

When the composition includes a chemotherapeutic agent, the chemotherapeutic agent can, for example, be selected from selected from the group consisting of busulfan, hexamethylmelamine, thiotepa, cyclophosphamide, mechlorethamine, uramustine, melphalan, chlorambucil, carmustine, streptozocin, dacarbazine, temozolomide, cisplatin, carboplatin, ifosfamide, methotrexate, azathioprine, mercaptopurine, fludarabine, 5-fluorouracil, vincristine, vinblastine, vinorelbine, vindesine, paclitaxel, docetaxel, podophyllotoxin, irinotecan, topotecan, amsacrine, etoposide, etoposide phosphate, teniposide, dactinomycin, doxorubicin, daunorubicin, epirubicin, bleomycin, plicamycin, mitomycin or any combination thereof.

When the composition includes a cytokine, the cytokine can, for example, be selected from the group consisting of IL-1, IL-2, IL-3, IL-4, IL-5, IL-6, IL-7, IL-8, IL-10, IL-12, IL-13, IL-15, IL-17, IL-18, IL-22, IL-23, IL-35, type I interferon, type II interferon, tumor necrosis factor-alpha, transforming growth factor-beta, granulocyte colony stimulating factor, granulocyte-monocyte colony stimulating factor, thymic stromal lymphopoietin or any combination thereof.

When the composition includes a chemokine, the chemokine can, for example, be selected from the group consisting of CC chemokines, CXC chemokines, C chemokines, CX3C chemokines or a combination thereof.

The compositions and methods described herein can avoid unregulated amplification of the immune system that can result in a systemic immune response accompanied by side effects including tissue destruction, an autoimmune response or inflammation of internal organs. Instead, the compositions and methods described herein can facilitate control of the immune response to the presence of bacteria at the site of the implanted medical device or biomaterial, such as by avoiding systemic effects, by avoiding the oxidative response often accompanying an immune response, or by minimizing the involvement or activation of neutrophils.

The compositions and methods described herein can reduce the bacterial titer at a site of an implant or implantation device. The compositions and methods described herein can prevent bacteria from adhering to or colonizing the site of administration by activating macrophages.

The compositions and methods described herein can target specific pathways involved in macrophage activation such as including, but not limited to the interferon signaling, interferon-γ, Janus-Activated Kinase (JAK), Signal Transducer and Activator of Transcription (STAT), Unfolded Protein Response (UPR), Mitogen Activated Protein Kinase (MAPK), Tumor Necrosis Factor (TNF), NF-KB, inflammasome-related, lipopolysaccharide (LPS), Wnt (canonical and noncannonical), nuclear receptor transrepression, TGF-f3 (and associated BMP molecules), SMAD calcium mobilization and DNA damage related pathways. Classical and alternate macrophage activation pathways can also be targeted by the present approach.

The compositions and methods described herein can help reduce or eliminate bacterial infections in several ways. A microenvironment can be provided such as to inhibit, prevent, or minimize bacterial colonization on an implantable device or biomaterial such as by inhibiting adhesion of bacteria to the device or material. A release of particles at the site of surgical implantation can promote a tunable and tightly regulated modulation of the immune response for the phagocytosis of bacteria.

The compositions and methods described herein can help reduce or prevent bacterial colonization on an implanted medical device or biomaterial. The compositions and methods described herein can modulate the localized immune response, and can be tailored to combat the presence of bacteria on an implanted medical device or biomaterial. The compositions and methods described herein can promote bacterial adhesion to a coated surface such that the surf ace can degrade, be released, or "peel off," to thereby accentuate the clearance of bacteria. The degradation can occur after a time sufficient to activate macrophages.

Particles

Particles that can be used with the compositions, coatings, implants and implantation devices can be either synthetic or manufactured from a naturally-occurring protein or one or more other molecules. The molecular composition can include one or more natural or engineered therapeutic cytokines, natural or engineered chemokines, natural or engineered antibodies, natural or engineered peptides (e.g., with or without nucleotides of any non-amino acid molecule conjugated to it), recombinant DNA molecules, or a combination of these. A biodegradable particle can include one or more of a polymer, which can comprise, but is not limited to a polysaccharide, carbohydrate, starch, cellulose, chitin, chitosan, lignin, gelatin, dextran, inulin, Poly(glycolic acid) (PGA), Poly(lactic acid) (PLA), Poly (Lactide-co-Glycolide) copolymer (PLGA), poly(D,L-glycolide) (PGA), poly(glycerol sebacate) (POSA), Poly(e-caprolactone), polyhydroxybutyrate (PHB), polyhydroxyvalerate (PHV), polydioxanone (PDS), poly(pyranose), poly(furanose), polyanhydride, polyorthoester, poly(hydroxyl acid), poly (lactone), poly (amino acid), poly(anhydride), poly(methane), poly (orthoester), poly (phosphazine), poly(phosphoester), poly (lacticco-glycolic) acid, poly(ether ester)s, synthetic poly(amino acids), polycarbonates, poly(hydroxyalkanoate)s, poly(caprolactone)s, poly(cianoacrylate), poly (alkylcianoacrylate), poly(ketal), poly(caprolactone), poly (acetal), poly(hydroxy-ester), poly(hydroxyl-alkanoate), poly(propylene-fumarate), poly poly(ester), poly(ethers), poly(carbonates), poly(amide), poly(siloxane), poly(silane), poly(sulfide), poly(imides), poly(urea), poly(amide-enamine), poly(organic acid), poly(electrolytes), poly(p-dioxanone), poly(olefin), poloxamer, inorganic or organometallic polymers, elastomer, or a derivative, or a combination of these.

A particle can include a polymeric resin such as a polypropylene, polycarbonate, polyurethane, polyvinyl chloride, nylon, polystyrene, polyethylene, polyethylene terephthalate, fluorinated polyethylene, polyvinyl alcohol, polyvinyl acetate, silicone, polyester or any combination thereof.

A particle can include zein, modified zein, casein, gelatin, gluten, serum albumin, collagen, actin, n-fetoproteiu, globulin, macroglobulin, cohesin, laminin, fibronectin, fibrinogen, osteocalcin, osteopontin, osteoprotegerin, or others, as will be appreciated by one skilled in the art In another embodiment the polymer may comprise cyclic sugars, cyclodextrins, synthetic derivatives of cyclodextrins, glycolipids, glycosaminoglycans, oligosaccharides, polysaccharides such as alginate, carageenan, chitosan, celluloses, chondroitin sulfate, curdlan, dextrans, elsinan, fuicellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, 20 poly (3-hydoxyalkanoate)s, such as poly(hydroxybutyrate), poly (3-hydroxyoctanoate) or poly(3-hydroxy fatty acids) or a combination of these. In another embodiment, the polymer may comprise chemical derivatives thereof (substitutions, additions, and elimination of chemical groups, for example, alkyl, alkylene, hydroxylation, oxidation, and other modifications routinely made by those skilled in the art), alone or in any combination with synthetic polymers.

A particle can comprise synthetically modified natural polymers, and may include cellulose derivatives such as alkyl celluloses, hydroxyalkyl celluloses, cellulose ethers, cellulose esters, nitrocelluloses, chitosan or a combination thereof. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt or any combination thereof.

A particle can comprise synthetic degradable polymers, which may include, but are not limited to polyhydroxy acids, such as poly(lactide)s, poly(glycolide)s, poly(ethylene terephthalate), poly(hydroxybutyric acid), poly(hydroxyvaleric acid), poly(pseudo amino acids), poly(amino acids), poly(hydroxyalkanoate)s, poly(anhydrides), poly(orthoester)s, and blends and copolymers thereof.

A particle can comprise a bioerodible polymer such as poly(lactide-co-glycolide)s, poly(anhydride)s, and poly(orthoester)s, which have carboxylic groups exposed on the external surface as the smooth surface of the polymer erodes, which may also be used. A particle can comprise a polymer containing labile bonds, such as polyesters.

A particle can have a density of about 0.3 to about 3.9 g/cm$^3$, Preferred embodiments include a particle having a density of about 0.35 g/cm$^3$, 0.6 g/cm$^3$, 1.1 15 g/cm$^3$, 1.51 g/cm$^3$, 2.2 g/cm$^3$, 2.45-2.5 g/cm$^3$, or 3.86 g/cm$^3$.

The particles can be made in whole or in part from inorganic, organic, magnetic, fluorescent, or radioactive material, or any combination of these. The particles can be made in whole or in part from latex, metals, silica, alumina, titania, glass, ceramic, polystyrene, melamine, PMMA, polylactide, dextran, or any combination thereof.

By way of example, inorganic metal particles can be made in whole or in part from gold, silver, palladium or platinum, or any combination of these. Inorganic silica particles can be made in whole or in part from $SiO_2$, aminated $SiO_2$ ($SiO_2$—$(R)_n$—$NH_2$), epoxy $SiO_2$ ($SiO_2$—$(R)_n$-EP), carboxylated $SiO_2$ ($SiO_2$—$(R)_n$—COOH), avidin $SiO_2$, streptavidin $SiO_2$, protein A coated $SiO_2$, fluorescent-blue $SiO_2$, fluorescent-red $SiO_2$, fluorescent-green $SiO_2$, or any combination thereof.

Inorganic alumina particles can be made in whole or in part from plain $Al_2O_3$, amino coated $Al_2O_3$, carboxyl coated $Al_2O_3$. Other functional groups can include albumin, protein A, epoxy, NHS, NT A, EDT A or others. The plain $Al_2O_3$ particles can be insoluble in water and insoluble in organic solvents. The plain $Al_2O_3$ can preferably have a specific gravity of 3.75-3.69 g/cm$^3$. The crystal structure can be crystalline, α-$Al_2O_3$ corundum phase. The surface area can preferably be less than 2-3 m$^2$/g and can be non-porous. The surface charge can be positive (pH≤9.3) or negative (pH≥9.3). The $Al_2O_3$ particles can have a density that of 1 g/cm$^3$ to 4 g/cm$^3$, The $Al_2O_3$ particles preferably have a density of 2.2 g/cm$^3$. The crystal structure can be amorphous or could be converted into crystalline state by heating.

Inorganic titania particles can be made in whole or in part from plain $TiO_2$, amino coated $TiO_2$, or carboxyl coated $TiO_2$. Other functional groups can include albumin, protein A, epoxy, NHS, NTA, EDTA or others. The plain $TiO_2$ particles can be insoluble in water and insoluble in organic solvents. The $TiO_2$ particles can preferably have a density of 2.2 g/cm$^3$. The crystal structure can be amorphous or can be converted into crystalline state anatase or rutile by heating. The surface charge can be positive (pH≤4.5) or negative (pH≥5). Particles made of titania can have the special property of being a strong oxidant of organic molecules.

Inorganic glass particles can be made in whole or in part from plain glass, precision glass, sieve calibration glass, high refraction index glass, hollow glass, or dyed glass. The refraction index of the high refraction index glass can preferably range from 1.90-2.00. The high refraction index glass particle size can range from 1-100 μm. More specifically, a high refraction index glass particle can be in the size range of 22±8.7%, 29±10.3%, 34.5±4.3%, 37.5±1.3%, 39.5±1.3%, 43.0±4.7%, 48±4.2%, 52.0±1.9%, 55.0±1.8%, 60.0±5.0%, 67.5±5.2%, 73.5±2.0%, 78.0±2.6%, 85.5±85.3%, 95.5±4.7%, 103.5±2.4%. Hollow glass particles can be made from borosilicate glass. The particles can be hollow, but non-porous. The true density of the C-PHGL (Corpuscular Plain Hollow GLass) can be size dependent; for instance, 25 11 μm, 18 μm, and 30 μm hollow glass beads have true densities of 1.1, 0.6, and 0.35 g/cm$^3$, respectively. Dyed glass can be made in whole or in part from high pure raw materials (in some instances, soda lime). The dyed glass can have a pure and shining surface. A dyed glass particle can preferably have a density of 2.45-2.50 g/cm$^3$. A dyed glass particle can have a chemical composition of 65% $SiO_2$, 13% $Na_2O$, 8% CaO and other minor components. The dyed glass particle can be free from lead oxide. A dyed glass particle can be red, yellow, green, blue, pink, fuchsia, purple, silver, gold, copper, black, or any other color.

Inorganic ceramic particles can be made in whole or in part from zirconium oxide. The zirconium oxide particle can be yttrium-stabilized. In some cases, ZrOY beads can be made in whole or in part from high purity Zirconia powder and is fully Yttrium stabilized to ensure extreme resistance to wear. The chemical composition of a zirconium oxide yttrium-stabilized particle can be $ZrO_2$—95.0%, $Y_2O_3$—5.0%. The specific weight can preferably be >5.9 g/cm$^3$. The hardness can preferably be Mohs≥8.0. The crushing strength can preferably be 15 KN.

The inorganic ceramic particle can be made in whole or in part from zirconium silicate. The chemical composition of a zirconium silicate particle can be $ZrO_2$—68.5%, $SiO_2$—31.5%. The density can preferably be 3.86 g/cm$^3$. The hardness can preferably be Mohs≥7.2. The melting point can preferably be >2500° K. The crushing strength can preferably be 710N.

Organic particles can be made in whole or in part with polystyrene, PMMA (polymethylmethacrylate), melamine (polymethylenemelamine), polylactide, or any combination thereof. An organic polystyrene particle can be aminated, carboxylated, coated with avidin, streptavidin, biotin, antibody or a fluorescent material. In the instance of a polystyrene particle made in whole or in part or coated with avidin, the avidin content can preferably be 14 μg/mg of solid particles, or 0.212 nmole/mg of solid particles.

In the instance of a particle made in whole or in part of melamine (polymethylenemelamine), the particle can be made from crosslinked melamine. The particle can preferably have a density of about 1.51 g/cm$^3$. The particle can be heat resistant up to 300° C. The particle can preferably have a refractive index of about 1.68. The surface of a melamine (polymethylenemelamine) can be terminated with a methylol group. The methylol group could be functionalized in a desired manner. A melamine particle can have an amino functional surface. The amino surface group can be NH or $NH_2$. The NH or $NH_2$ group can be at every nm$^2$. For instance, a particle with 1 μm diameter can have at least 3,000,000 surface amino groups. A melamine particle can be modified to have a high density of carboxy functional groups. A melamine particle having a carboxy functional group can preferably have a density of 1.51 g/cm$^3$. The refractive index can be 1.68. A melamine particle having a carboxy functional group can have a C.V. of <3%. A melamine particle having a carboxy functional group can preferably have high temperature stability up to 250° C.

In the instance of a particle made in whole or in part of polylactide, the particle can be plain, aminated, carboxylated, can include collagen or can be dyed a fluorescent or non-fluorescent color.

A particle can be made in whole or in part of a magnetic material. In one instance, the magnetic material can include silica, polystyrene, dextran, or any combination thereof. A functional magnetic particle can include any one or any combination of the following: silanol, carboxyl, amino, chloromethyl, streptavidin, biotin, avidin, protein A, antibody, or albumin. A magnetic particle can be PEGylated, COOH terminated PEGylated, or NH2 terminated PEGylated. A magnetic particle can include a fluorescent material. A magnetic particle can include dextran, aminated $NH_2$, carboxylated COOH, avidin, streptavidin, biotin, or protein A.

A particle can be made in whole or in part from a radioactive material. A radioactive particle can include oxide, polymer, or a magnetic material. A radioactive particle can include Holmium-166. In one instance, the particle can be $^{166}Ho_2O_3$—$SiO_2$. A radioactive particle can include Praseodymium-166. In one instance, the particle can be $^{142}Pr_2O_3$—$SiO_2$.

A particle can include a fluorescent material. In the instance of a particle involving a fluorescent material, the material can be yellow, light yellow, acridine yellow, red, nile red, far red, Texas red, pink, purple, violet, blue, sky blue, light blue, nile blue, orange, acridine orange, green, rhodamine B, FITC any other fluorescent color, or any combination thereof. The intensity of the fluorescent material can be of low intensity, medium intensity or high intensity.

The particles can have functional surfaces. The functional surfaces can be useful for coupling of DNA, oligonucleotides, oligopeptides, proteins, lectins and antibodies. The functional surfaces can comprise an amine, epoxy, carboxyl, avidin, streptavidin, protein A, fluorescent material, or a combination thereof. The particle surface can be plain, or include biotin, streptavidin, or antibody finishes, or any combination thereof.

The particles can be doped with other elements. The doped elements could be distributed uniformly, internally or externally. The particles can have homogenous or heterogeneous surfaces. The particles can have smooth surfaces or rough surfaces, or a combination. A particle may contain air-bubbles. In some cases, a particle can be free from foreign particles, glass fragments, or other impurities.

The particles disclosed herein that are suitable for administration or incorporation into a composition or coating can fall within a range of sizes. As one illustration, the particles can have a diameter ranging from about 0.01 μm to about 15 μm. In one illustration, the particles can have a diameter that is less than or equal to 10 μm, less than or equal to 1 μm, less than or equal to 0.5 μm, or less than 15 or equal to 0.1 μm. The particles can vary in size, can include particles of multiple-sizes, or can be uniform in size. Any sized particle suitable for triggering phagocytosis can be suitable for use.

The particles can range in size from 1 to 1000 nm. More specifically, the nanoparticles can average in size from about 1 nm, 2 nm, 5 nm, 10 nm, 15 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 25 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, to about 1000 nm.

The particles can range in size from 1 μm to 100 μm. More specifically, the microparticles can average in size from about 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10.0 μm, 15.0 μm, 20.0 μm, 25.0 μm, 30.0 μm, 35.0 μm, 40.0 μm, 45.0 μm, 50.0 μm, 55.0 μm, 60.0 μm, 65.0 μm, 70.0 μm, 75.0 μm, 80.0 μm, 85.0 μm, 90.0 μm, 95.0 μm, to about 100.0 μm.

The particles can include a mixture of synthetic or naturally-occurring proteins or other molecules. The particles can be available as a dry powder, or suspended in aqueous media. In one instance, the aqueous media can be deionized water. A coated particle can be prepared by passive adsorption or covalent coupling. A particle can be prepared by emulsion and/or emulsion-free polymerization.

The particle shape or surface can be of any molecular composition that inhibits or prevents bacterial colonization of an implant. The shape or surface of the particle can attract bacteria to the particle surface rather than the medical implant surface. The particles or surface of the particles can be ionically charged. The surface can be positively charged or negatively charged. The particles can be generally spherical in shape. The particles can be perfectly spherical. The particles can be substantially rod shaped, cone shaped, cylindrical, cuboidal, spherical, square, rectangular, planar, ovoid, any other suitable shape, or any combination thereof. The particles can range in sphericity from 98-100%. The particles can range in sphericity from ≥95%. The surface of particles can be smooth. The average surface roughness ($R_a$, measured in microns) can be below 0.2, below 0.1, below 0.05, or below 0.01. The surface of the particles can be rough. As one illustration, the average surface roughness ($R_a$, measured in microns) can be greater than 0.2, greater than 0.3, greater than 0.4, greater than 0.5, greater than 1, greater than 5, or greater than 10. As used herein, average surface roughness is a height parameter defined as the average deviation of the surface profile from the mean line.

The particle surface can include a surface that inhibits or prevents bacterial propagation. The particle surface can include a surface that is configured to attract bacteria, such as to promote bacterial adhesion. Examples of surface components that can increase bacterial adhesion can include, but are not limited to fibronectin, albumin, fibrinogen, thrombin, thrombospondin, or platelet protein.

The inhibition or prevention of bacterial colonization of an implant can also be facilitated by one or more agents implanted with the particles. The particles can include or be implanted with an added agent such as a bactericidal agent (e.g., an antimicrobial), antibiotic, or antibiotic conjugate. Examples of bactericidal agents can include but are not limited to penicillin, streptomycin, cephalosporins, bacitracin or any combination thereof. Examples of antibiotics can include, but are not limited to, β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol, or any combination thereof. Other added agents can be used in combination with one or more additional bactericidal agents, antibiotics, or antibiotic conjugates.

Methods of Treatment

One effect of the present compositions and coatings can be to prevent or minimize the colonization of bacteria on a surface of a biomaterial implant such as by inhibiting adhesion of the bacteria to the implant surface. Another effect can be to encourage bacterial adhesion to a particle that is upon or associated with an implant. Another effect can be to regulate the amplification of an adaptive immune response to infection.

The present inventors have discovered that an implant coated with a particle formulation including a biodegradable or stable micro-particle or nano-particle formulation composed of natural or synthetic materials can help achieve one or more of the aforementioned effects. The formulation can be present in a uniform or layered format configuration such as to further inhibit or prevent bacterial colonization or modulate the immune response.

Thus, one aspect of the invention is a method of reducing a microbial infection at a site in an animal in need thereof, that includes locally administering to the site an effective amount of a composition comprising particles having a diameter of about 1.0 nm to about 100 µm, to thereby reduce microbial infection at the site in the animal. The particles can inhibit bacteria from adhering to or colonizing the site. In some embodiments, the composition is configured to biodegrade after activating macrophages without substantial activation of neutrophils.

The present compositions and methods can provide particles that are locally administered to a surgical site. Local administration can include coating the surface of an implant with particles. Local administration can include injecting particles such as into an infected site or into a surgical site.

The administration of an added agent can be systemic or local. When administration is local, an added agent can be part of a particle composition or be coated on the outside of a particle, co-administered into the site of the implant, or encapsulated within a particle. When the added agent is encapsulated within a particle, it can be released upon disintegration of a one or more of the particles or coating layers. When the particle disintegration releases an added agent, the disintegration can either degrade spontaneously or be caused by phagocytosis by macrophages.

A particle can facilitate a localized, non-systemic amplification of an adaptive active immune response. The localized amplification can be attenuated and primarily targeted to macrophage activation with minimal involvement of the neutrophils through a timed degradation of the particles. The timed degradation can up-regulate in vivo bactericidal mechanisms that are not reliant on the oxidative stress response. The particles on the surface of the implanted device can up-regulate the phagocytotic activities of the macrophages. The particles can induce macrophage infiltration into the implant site. The cell mediated response facilitated by the particles can magnify the local cell mediated response such as by increasing phagocytosis and bacterial clearance from the site of infection. The process of localized particle-mediated immune response need not pharmacologically influence any oxidative burst associated with any subsequent phagocytosis of bacteria or pathogens in the vicinity of the biomaterial implant. Thus, the neutrophil response can be down-regulated, or neutrophil involvement can be minimal or only a secondary process. In some embodiments, there is substantially no neutrophil response associated with the administration of a particle composition or implant coated by a particle composition.

The localized, non-systemic amplification of the adaptive active immune response can be achieved in a variety of ways. In general, the immune amplification can be localized to the region of the implanted composition or coated implantation device. The prevention or inhibition of bacterial infections caused by the localized response can be restricted to macrophage-mediated mechanisms. The immune amplification of an adaptive active immune response can involve a biochemical, signaling pathway, or metabolic pathway, or any combination thereof. The immune amplification can be trigged by transcription, translation, silencing, or enhancing of genes. The biodegradable particles can degrade spontaneously following phagocytosis.

The degradation of the particles can be biologically-induced or chemically-induced. Biologically-induced degradation can occur, for example, by enzymes or metabolism. Chemically-induced degradation can occur, for example, by dissolution in the physiological environment, or by pH-mediated breakdown.

The implant can be dipped into a suspension of particles before insertion so that the implant can be coated with particles before implantation. The particles can be administered after administration of the implant.

The present coatings and methods can include use of layers of particles or a 30 single coating of a particle composition. Individual layers or coatings can break down in the body. The particle layers or coating can be configured to disintegrate, "peel off," or otherwise disassociate such as at specified time intervals. Such particle layers, or coatings can inhibit or prevent bacteria from adhering to or colonizing an implant surface. The peeling off process can be configured to occur continuously or in a stepwise fashion. The particles in the layer or coating can attract bacteria to the particle surface rather than to the implant. Peeling or disintegration of particle layers or coatings can inhibit bacterial colonization of the implant, such as by inhibiting or preventing the bacteria from surrounding the implant with a biofilm. Preventing formation of a biofilm on the implant can be particularly advantageous because biofilms frequently are not effectively penetrated by antibiotic agents. Further, bacteria encased in a biofilm often cannot be cleared or eliminated by macrophages.

A regulated disintegration of the particle coating, such as described above, can promote a highly regulated and timed localized immune response. Particle disintegration can occur in one phase or, in an example, in at least two phases, such as an initial phase of rapid disintegration followed by a phase of slower disintegration. The first phase of rapid disintegration can result in a magnified immune response to help destroy the bacteria. The particles can magnify a local cell mediated immune response, for example, by increasing bacterial killing, phagocytosis, or bacterial clearance from the infection site. However, in order to prevent systemic upregulation of the immune response, the immune response can be returned to its more quiescent state quickly such as by slowing down or even ceasing the release of the particles from the implant surface such as after a certain specified period of time. Thus, the amount or disintegration properties of particles employed can be tailored to initiate a localized immune response (e.g. via macrophages) but avoid a systemic immune response.

The particles can be coated with specific molecules that can mimic the presence of bacteria and thus, accelerate a localized immune response. Activation of an adaptive active immune response can occur in specific cells in the blood stream and not to macrophages alone. In one illustration, the timed release of the particles in a coating or from a surface of the biomaterial implant does not directly accelerate, induce, or modulate a neutrophil-mediated oxidative burst. The timed release of the particles from one or more surfaces of the biomaterial implant can inhibit a neutrophil-mediated oxidative burst.

The particles can be applied to the surface of an implantable medical device or biomaterial such that the particles can be released across desired time spans. The particles can be released over a specified time period, such as an about one week time span, over a period ranging from about one day to about seven days, over an about a 24-hour period, over a period of about 4 hours, or the particles can be released in less than about 4 hours. Multiple layers of degradable particle-containing coatings can be applied so that degradation rates of respective layers can differ, such that the overall degradation rate of the aggregate multiple layers can vary over time.

The degradation rate of the small particles can be specified or adjusted such as to prevent long term effects on the normal immune response at the implant site. The coating and particle composition can be composed of assorted available materials that can be configured to refine the character of the local response. The particle coating can be used in combination with a compound, such as an antimicrobial compound, that can be released at least partially concurrently. Such a combination can accentuate both the antimicrobial properties and local cell-mediated immune response of such a composite coating, and thereby improve clearance of bacteria.

One or more coated surfaces of the biomaterial implant can be used to promote adhesion of bacteria such as at a specified region. The particles present in the coating can act as a binding surf ace for bacteria, thereby reducing the bacterial numbers available for binding directly to an implant surface. A bacteria-bound particle can be of a size capable of being phagocytosable by macrophages, facilitating bacterial clearance from the surrounding bodily tissues. Once phagocytosed, the particles can be rapidly degraded within the phagosomes (e.g., macrophages) along with any bound bacteria. Thus, the particles can reduce the bacterial titer in the vicinity of the biomaterial implant. Such induction of phagocytosis can also help decrease or minimize the involvement of neutrophils and help avoid a neutrophil-induced oxidative burst.

The particles can be configured to provide one or more appropriate surf ace characteristics, such as a desired surface charge or hydrophobicity, to facilitate bacterial binding. The particles can have a physical or chemical surface configuration, density, or porosity (e.g., porous or non-porous) such as to facilitate bacterial binding. The particles can be released from the biomaterial surface, for example, to carry particle-bound bacteria away from an implant's surface, without being dependent on cell-mediated (e.g., macrophage or neutrophil) immune mechanisms.

The present inventors have recognized and believe that specific, regulated immune responses in the presence of particles can be effective to control bacterial infections with little or no detrimental systemic side-effects. An effective bacterial treatment can be achieved by administering biocompatible particles to facilitate a localized, non-systemic amplification of adaptive, active local immune response directed towards the attenuation or neutralization of bacterial infection at the site of surgical implants.

The present subject matter can be used in conjunction with various types of iomaterial implants, including surgical meshes, vascular grafts, catheters, orthopedic device implants (e.g., artificial joints), dental implants, bone fixation rods, plates, screw, etc. or any other medical implants having an incidence of bacterial infection.

The following examples are provided in order to demonstrate and further illustrate certain embodiments and aspects of the present invention and are not to be construed as limiting the scope thereof.

Example 1: Degradable Micro- or Nano-Particles Cultured with Mouse Macrophage Cell Lines Cell line: Mouse macrophage cell line RAW 264.7 was purchased from ATCC. The RAW 264.7 line was established from a tumor induced by Abelson murine leukemia virus. RAW 264.7 cells are negative for surface immunoglobulin, 1a, and Thy-1.2. These cells do not secrete detectable virus particles. RAW 264.7 cells were seeded onto 75 cm2 flasks at a subcultivation ratio of 1:3 to 1:6. Medium was replaced or added every 2 to 3 days. Cells were not passaged for more than 30 days.

Cell culture: RAW 264.7 cells were cultured in Dulbecco's Modified Eagle's Medium (DMEM, Invitrogen) supplemented with 10% fetal bovine serum (Invitrogen). Subcultures were prepared by scraping. Cells were maintained at 95% air, 5% $CO_2$ at a temperature of 37.0° C.

Micro- or nano-sphere incubations: Polystyrene microspheres or nanospheres (Corpuscular, Inc.) were tested for endotoxin levels and were confirmed to be <0.05 EU/ml prior to use using the Limulus amebocyte lysate (LAL) assay (WuXi AppTec). RAW 264.7 cells were seeded at 30% into 6-well plates one day prior incubations. Nano-spheres of 0.1 μm or 0.5 μmin size or micro-spheres of 1.0 μm in size were used for incubations. Particle densities of $2.5 \times 10^5$, $5.5 \times 10^5$, $7.5 \times 10^5$, $1.0 \times 10^6$ per $cm^2$ were introduced into wells. The cells were gently agitated during the incubation and were incubated for various periods of time. In some examples, the cells were incubated with the micro- or nano-spheres for up to 3 days before harvesting. In other examples, the micro- or nano-spheres were removed after 12 hours, and the growth medium was replaced every 12 to 15 hours for up to 3 days before harvesting. In other examples, the micro- or nano-spheres were removed after 24 hours, and the growth medium was replaced every 24 hours for up to 3 days before harvesting.

Microscopy: After incubation with micro- or nano-spheres, RAW 264.7 cells were observed. Images of the macrophage phagocytic response were taken using a Zeiss Axiovert 40 CPL microscope. Imaging was performed using a 40× objective in combination with a phase contrast condenser.

Western blot analysis: Fifteen percent SOS-PAGE gels were used for western blot analysis. The XCell II Blot apparatus (Invitrogen) was utilized. Suitable antibodies can be obtained from polyclonal sera, monospecific sera or from monoclonal antibody culture. Techniques for producing and processing monoclonal and polyclonal sera are abundantly known in the art (e.g. Reinherz et al. (1979) J. Immunol. 123, 1312, Ritz et al. Nature (1980) 283, 583, and Mayer and Walter, eds. Immunochemical Methods in Cell and Molecular Biology, Academic Press, London, 1987). Animals suitable for raising the antibodies are e.g. cows, rabbits, mice or chickens.

A mouse antibody recognizing MIP-3a was utilized and produced a 12.2 kDa band (+/−5 kDa) after polyacrylamide gel electrophoresis. A mouse antibody recognizing CXCL-10 produced a 10.9 kDa band (+/−5 kDa). A mouse antibody recognizing CCL-22 produced a 10.7 kDa band (+/−5 kDa). A goat anti-mouse HRP-conjugated secondary antibody (Invitrogen) was also used.

Enzyme-linked immunosorbent assay (ELISA): Standard ELISA techniques such as direct, indirect, competitive, or noncompetitive immunoassays were employed (see, e.g., Oellerich, M. 1984. J. Clin. Chem. Clin. Biochem 22:895-904). Prior to use in ELISA experiments, serum was removed from culture media using the ProteoPrep 20 Plasma Immunodepletion Kit (Sigma-Aldrich). Mouse MIP-1a and MIP-3a ELISA plates were assembled using non-commercial reagents. Recombinant mouse MIP-1a and MIP-3a were used as standards. End-point assays were read on a BMG microplate reader (Germany). RAW 264.7 cells were incubated with various sized particles for twelve hours.

Rates of utilization of glucose and glutamine and lactate production: To investigate glucose, glutamine and lactate production by RAW 264.7 cells, cells were first either unexposed to particles, or were exposed to particles ranging in size 20 from 0.1 to 1.0 μm. Medium was removed from the cells at various time points (0.5 ml) and was diluted with deionized water (0.5 ml). The diluted medium was injected into a Kodak Biolyzer for analysis. The analyses were performed over a 72 hour period in order to track the metabolic status of the cells.

Example 2: Degradable Micro- and Nano-Particles Trigger a Transitory, Tunable Response that is Localized to the Site of Injection in Animals Animal Studies: 250-300 g Sprague Dawley rats were anesthetized with 75 mg/kg ketamine and 10 mg/kg xylazine. Fur was shaved above each quadriceps muscle. Particles were injected in 5 μl to 40 μl amounts in 5 locations in both muscles at a 1:100 or 1:50 dilution. Polystyrene microspheres (1.0 μM, 25 mg/ml) were first sterilized in 80% ethanol by three 50 min centrifugation steps followed by three washes in sterile PBS. The particles were then resuspended in sterile PBS at a concentration of 2.5 mg/ml. Prior to injection, the particles were further diluted 1:50 and 1:100 in sterile PBS. After 3 days, rats were anesthetized with 75 mg/kg ketamine and 10 mg/kg xylazine. The muscles were removed quickly, snap frozen into cold isopentane, placed in a tube, and further frozen in liquid nitrogen. Blood was collected from the heart, and the animal was euthanized via exsanguination by removal of the heart. Heart blood was placed in a heparinized tube, centrifuged at 2,500 rpm for 25 min. Plasma was removed and frozen at −80° C. Control animals were either injected with PBS or taken out of the cage and returned without injection. The latter control was to normalize for any stress response that may be associated with handling the animal alone.

Histology: Cross-sections of 10 μm-12 μm thickness were cut from quadriceps on a cryostat (Leica Microsystems, Nusslock, Germany) at −20° C. Each muscle was then stained with hematoxylin and eosin for general morphology (see, 15 e.g., Snow, L M. 2012. Am. J. Phys. Med. Rehab.).

Microscopy: Images of the histology slides were taken using a Nikon N-Storm inverted microscope. 40× and 60× objectives were used to locate the particles in the vicinity of activated macrophages.

Enzyme-linked immunosorbent assay (ELISA): A standard ELISA technique similar to that explained above was performed on circulating blood of treated (micro- and nano-particle injection) and untreated (control) animals. In order to minimize interference with the final colorimetric signal, excess serum was removed using the ProteoPrep 20 Plasma Immunodepletion Kit as described before. ELISA plates were prepared using rat MIP-1a and MIP-3a antibodies. End-point assays were performed using a BMG microplate reader.

Results

Micro- or Nano-Particles Induce Phagocytosis, Induce Classical or Alternate Pathway Immune Response Phase-contrast microscopy of RAW 264.7 confirmed induction of phagocytosis of particles 10 μmin size after 24 hours (FIG. 1). An increased number of particles were phagocytosed by the cells when higher particles densities were incubated with the cells. For example, a greater number of particles were phagocytosed by the RAW 264.7 cells when incubated with micro- or nano-particles at a density of $10.0 \times 10^5$ (FIG. 1F) than when cells were incubated with micro- and nano-particles at a density of $7.5 \times 10^5$ (FIG. 1E). Similarly, a greater number of particles were phagocytosed by the RAW 264.7 cells when incubated with micro- and nano-particles at a density of $7.5 \times 10^5$ (FIG. 1E) than when cells were incubated with micro- and nano-particles at a density of $5.0 \times 10^5$ (FIG. 1D). A greater number of particles were phagocytosed by the RAW 264.7 cells when incubated with micro- or nano-particles at a density of $5.0 \times 10^5$ (FIG. 1D) than when cells were incubated with micro- or nano-particles at a density of $2.5 \times 10^5$ (FIG. 1C). RAW 264.7 cells incubated in the absence of particles showed no phagocytotic activity (FIGS. 1A & B).

Figure 8A:
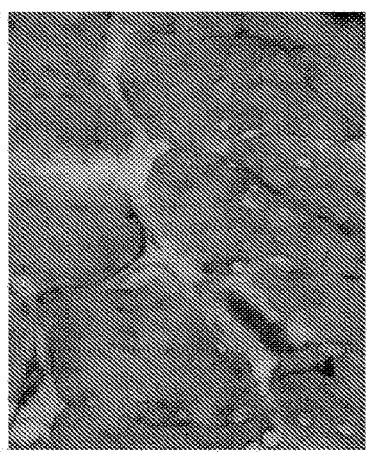
FIGS. 8A-8E shows images of rat quadriceps slices with phagocytosed microparticles.
Figure 8B:
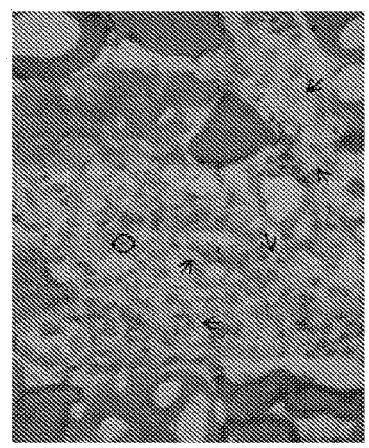
Figure 8C:
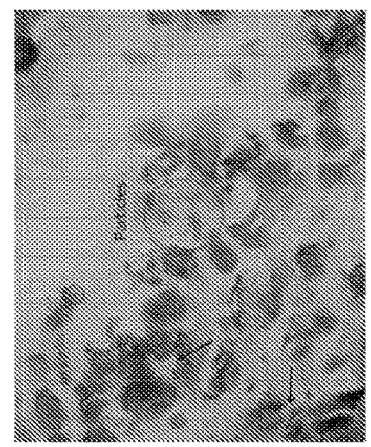
Figure 8D:
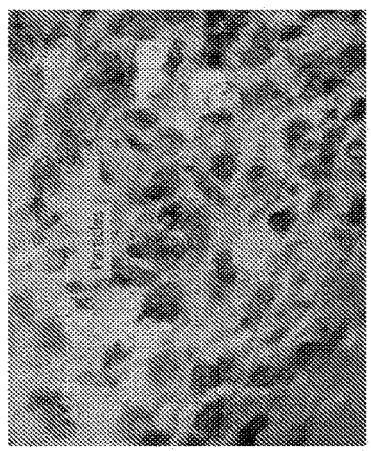
Figure 8E:
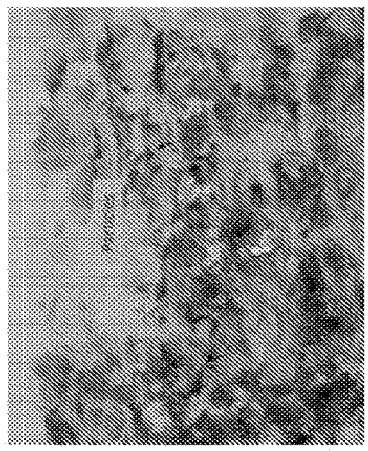

Histopathological examination of tissue section from sites injected with particles (FIG. 8B-E) demonstrated a marked influx of macrophages without increased cellularity or evidence of inflammation in tissues adjacent to the injection tracts when compared to controls (FIG. 8A). Macrophages in the presence of particles within the tissues showed intracellular, phagocytosed particles and evidence of "activation" (FIG. 8B-E). Activated macrophages exhibit less dense Nuclei and areas of foamy cytoplasm with evidence of intracellular phagocytosed particles as compared to inactive macrophages. The accumulation of activated macrophages with evidence of phagocytosed particles in the local injection site response was predominated by activated macrophages with minimal to absent neutrophils. Few if any macrophages were present in tissues outside the areas injected with particles supporting the induction of a local activation and mobilization of macrophages to the area injected with the particles, without distant effects (FIG. 8B-E).

Figure 2:
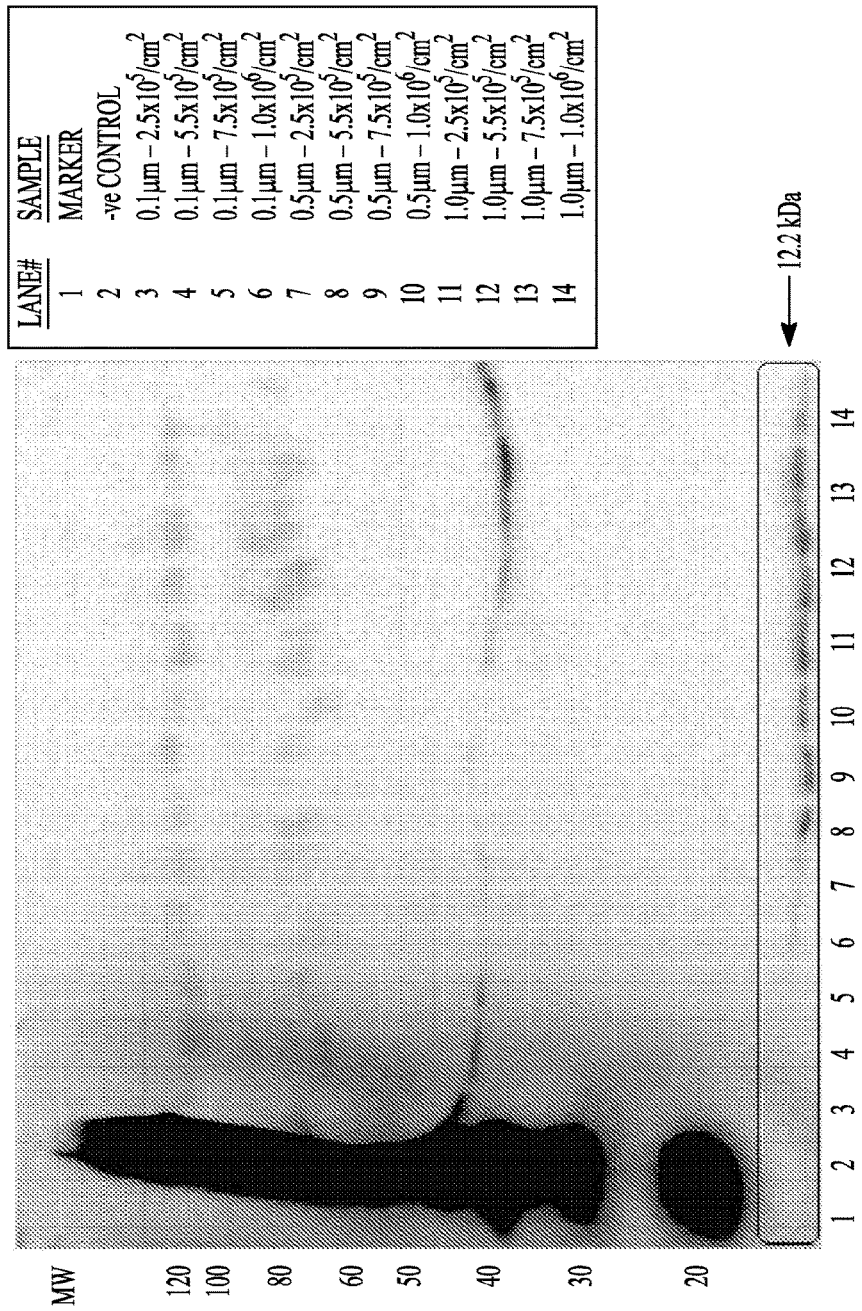
FIG. 2 shows the expression of MIP-3a by Western blot analysis. Lane 1 shows a protein molecular weight marker. Lane 2 shows a negative control, where the sample was taken from cells incubated in the absence of particles. Lanes 3-6 show the results from samples taken from cells incubated with 0.1 µm particles. In lane 3, cells were incubated for 24 hours with particles at a density of $2.5\times10^5$ particles/cm$^2$. In lane 4, cells were incubated for 24 hours with particles at a density of $5.5\times10^5$ particles/cm$^2$. In lane 5, cells were incubated for 24 hours with particles at a density of $7.5\times10^5$ particles/cm$^2$. In lane 6, cells were incubated for 24 hours with particles at a density of $1.0\times10^6$ particles/cm$^2$. Lanes 7-10 show the results from samples taken from cells incubated with 0.5 µm particles. In lane 7, cells were incubated for 24 hours with particles at a density of $2.5\times10^5$ particles/cm$^2$. In lane 8, cells were incubated for 24 hours with particles at a density of $5.5\times10^5$ particles/cm". In lane 9, cells were incubated for 24 hours with particles at a density of $7.5\times10^5$ particles/cm$^2$. In lane 10, cells were incubated for 24 hours with particles at a density of $1.0\times10^6$ particles/cm$^2$. Lanes 11-14 show the results from samples taken from cells incubated with 1.0 µm particles. In lane 11, cells were incubated for 24 hours with particles at a density of $2.5\times10^5$ particles/cm$^2$. In lane 12, cells were incubated for 24 hours with particles at a density of $5.5\times10^5$ particles/cm$^2$. In lane 13, cells were incubated for 24 hours with particles at a density of $7.5\times10^5$ particles/cm$^2$. In lane 14, cells were incubated for 24 hours with particles at a density of $1.0\times10^6$ particles/cm$^2$.
Figure 3:
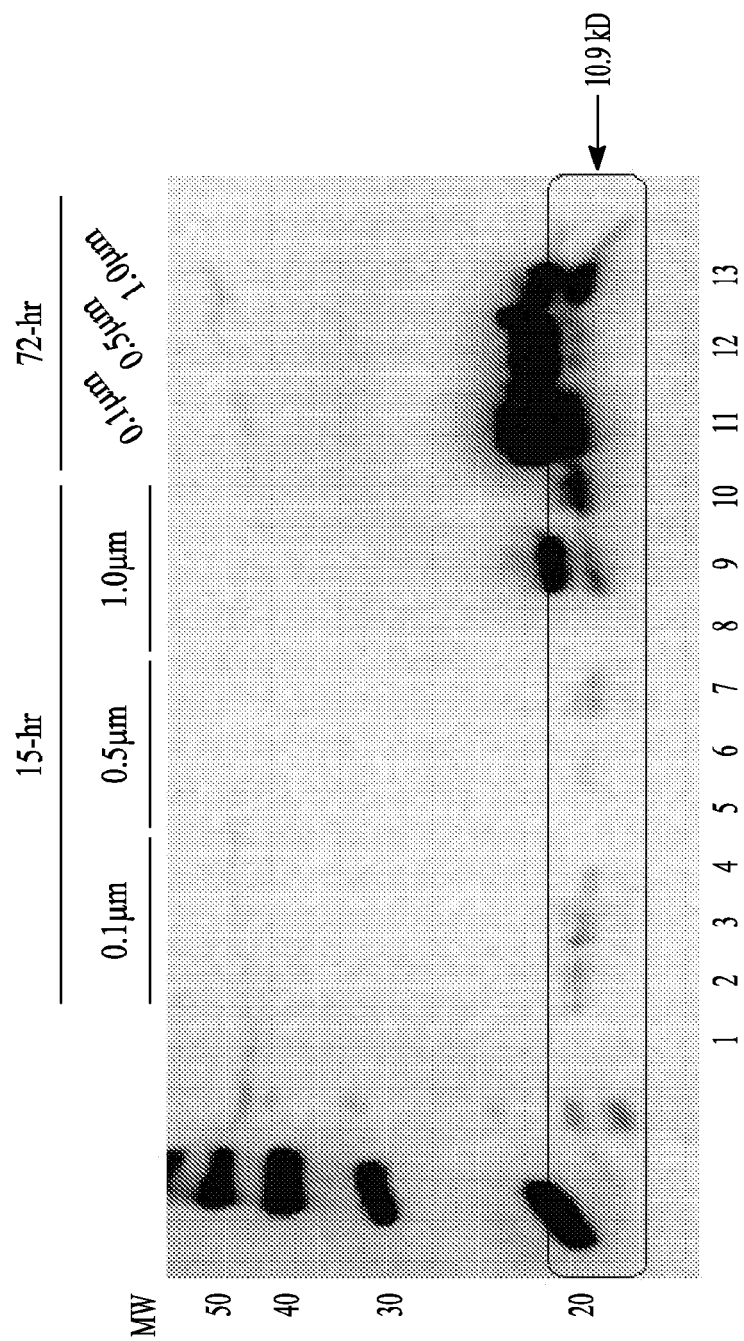
FIG. 3 shows the expression of CXCL-10 by Western blot analysis. The protein molecular weight marker can be shown on the far left side. Lane 1 shows a negative control, where the sample was taken from cells incubated in the absence of particles. In lanes 2-4, cells were incubated for 15 hours with 0.1 µm particles prior to Western blot. In lanes 5-7, cells were incubated for 15 hours with 0.5 µm particles prior to Western blot. In lanes 8-10, cells were incubated for 15 hours with 1.0 µm particles. In lanes 2, 5, and 8, cells were transiently cultured with particles for a total of 24 hours. In lanes 3, 6, and 9, cells were transiently cultured with particles for 48 hours. In lanes 4, 7, and 10, cells were transiently cultured with particles for 72 hours. In lanes 11-13, cells were incubated with particles for 72 hours. In lane 11, the particle size was 0.1 µm, 0.5 µm in lane 12, and 1.0 µm in lane 13.
Figure 4:
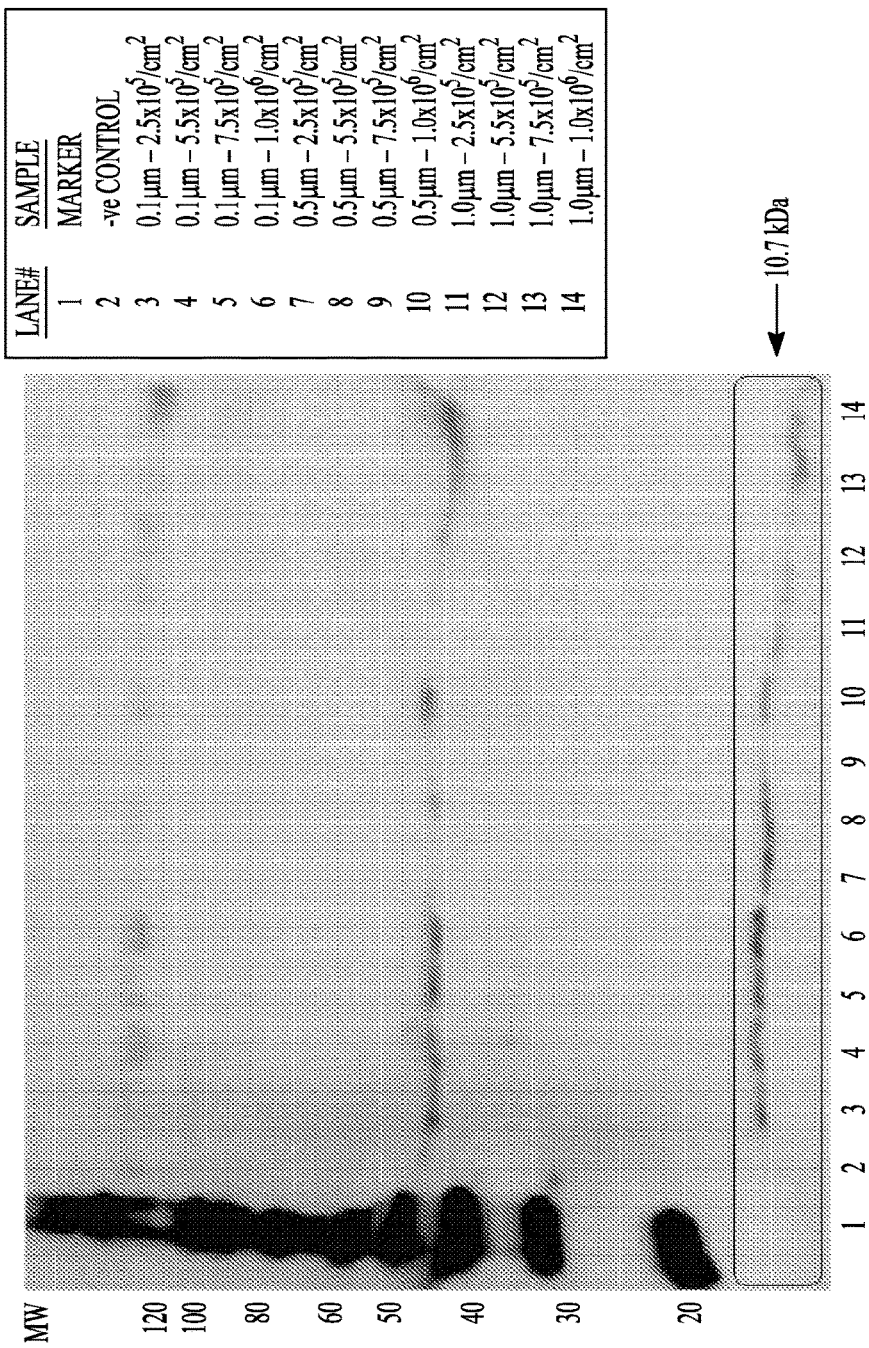
FIG. 4 shows the expression of CCL-22 by Western blot analysis. Lane 1 shows a protein molecular weight marker. Lane 2 shows a negative control, where prior to analysis, the sample was taken from cells incubated in the absence of particles. Lanes 3-6 show the results from samples taken from cells incubated with 0.1 µm particles. In lane 3, cells were incubated for 24 hours with particles at a density of $2.5\times10^5$ particles/cm$^2$, in lane 4 at a density of $5.5\times10^5$ particles/cm$^2$, and in lane 5 at a density of $7.5\times10^5$ particles/cm$^2$. In lane 6, cells were incubated for 24 hours with particles at a density of $1.0\times10^6$ particles/cm$^2$. Lanes 7-10 show the results from samples taken from cells incubated with 0.5 µm particles. In lane 7, cells were incubated for 24 hours with particles at a density of $2.5\times10^5$ particles/cm$^2$, in lane 8 at a density of $5.5\times10^5$ particles/cm$^2$, and in lane 9 at a density of $7.5\times10^5$ particles/cm$^2$. In lane 10, cells were incubated for 24 hours with particles at a density of $1.0\times10^6$ particles/cm$^2$. Lanes 11-14 show the results from samples taken from cells incubated with 1.0 µm particles. In lane 11, cells were incubated for 24 hours with particles at a density of $2.5\times10^5$ particles/cm$^2$, in lane 12 at a density of $5.5\times10^5$ particles/cm$^2$, and in lane 13 at a density of $7.5\times10^5$ particles/cm". In lane 14, cells were incubated for 24 hours with particles at a density of $1.0\times10^6$ particles/cm$^2$.

Western blot analysis indicated the induction of both classical and alternate immune response pathways (FIGS. 2-4). For example, to investigate the classical immune response, the expression of MIP-3a was observed after RAW 264.7 cells were incubated with micro- or nano-particles for 24 hours (FIG. 2). Particle size had a greater effect on MIP-3α expression than did particle density (FIG. 2). For example, the expression of MIP-3α was investigated when cells were incubated with particles 0.1-1.0 μmin size (FIG. 2). Cells were incubated with particle densities of $2.5 \times 10^5$, $5.5 \times 10^5$, $7.5 \times 10^5$, or $1.0 \times 10^6$ per cm². MIP-3α expression was largely unaffected by the particles of 0.1 μmin size (FIG. 2, lanes 11-14). Similarly, MIP-3α expression was largely unaffected by the particle density when the particles were 0.1 μmin size (FIG. 2, lanes 3-6). The expression of MIP-3α was also investigated when cells were incubated with particles of 0.5 μmin size at particle densities also ranging from $2.5 \times 10^5$ to $1.0 \times 10^6$ per cm² (FIG. 2, lanes 7-10). MIP-3α expression increased at all particle densities when the particle size was 0.5 μm (FIG. 2, lanes 7-10). Similarly, when cells were incubated with particles of 1.0 μm in size, MIP-3α expression increased at all particle densities (FIG.

2, lanes 11-14). Expression of MIP-3α increased to similar levels when the particle size was either 0.5 μm or 1.0 μm (FIG. 2, lanes 7-14).

In another example, to further investigate the classical immune response, the expression of CXCL-10 was investigated by Western blot analysis. RAW 264.7 cells were transiently exposed to micro- or nano-particles. Cells were exposed to particles for 72 hours (FIG. 3, lanes 11-13) or particles were removed after 15 hours, and fresh particle-free medium was added every 12-15 hours. Transiently exposed cells were cultured for a total of 24 hours (FIG. 3, lanes 2, 5, and 8), 48 hours (FIG. 3, lanes 3, 6, and 9), or 72 hours (FIG. 3, lanes 4, 7, and 10). When cells were exposed to particles for 72 hours, expression of CXCL-10 was increased irrespective of particle size in comparison to cells not exposed to particles (FIG. 3, lanes 11-13). When cells were exposed to particles and withdrawn after 15 hours, the expression of CXCL-10 was not greatly increased when particles were 0.1 or 0.5 μmin comparison to non-exposed cells (FIG. 3, lanes 1-7). When cells were exposed to particles 1.0 μmin size for 15 hours, an increase in CXCL-10 expression was seen after 48 to 72 hours (FIG. 3, lanes 8-10). In general, expression of CXCL-10 is primarily limited to cells exposed to micro- or nano-particles for prolonged periods of time (FIG. 3, lanes 8-13).

To investigate the induction of the alternate immune response pathway, the expression of CCL-22 was investigated by Western blot analysis. The expression of CCL-22 was investigated after RAW 264.7 cells were incubated with micro- or nano-particles for 24 hours (FIG. 4). Again particle size had a greater effect on expression than did particle density (FIG. 4). For example, expression of CCL-22 increased as compared to the negative control (e.g. RAW 264.7 cells not incubated with particles) when cells were incubated with particles of 0.1 μm size (FIG. 4, lanes 3-6). Although expression was slightly higher when cells were incubated with 0.1 μm particles at a density of $1.0 \times 10^6$, overall, expression of CCL-22 was largely unaffected by density when the particles were 0.1 μmin size (FIG. 4, lanes 3-6). In another example, RAW 264.7 cells were incubated with 0.5 μm sized particles also at densities ranging from $2.5 \times 10^2$ to $1.0 \times 10^6$ per cm² (FIG. 4, lanes 7-10). When particles were 0.5 μmin size, expression of CCL-22 was increased when compared to the negative control (FIG. 4, lanes 2 & 7-10). In another example, cells were incubated with particles that were 1.0 μmin size at densities ranging from $2.5 \times 10^5$ to $1.0 \times 10^6$ per cm². When cells were incubated with particles 1.0 μm in size, expression of CCL-22 was increased in comparison to cells that had not been incubated with particles, and seemed to be largely unaffected by particle density (FIG. 4, lanes 11-14). Overall, expression of CCL-22 expression was greatest when cells were incubated with particles 0.1 μmin size (FIG. 4, lanes 3-6). Expression of CCL-22 decreased as the particle size increased (FIG. 4). Particle density had little to no effect regardless of particle size (FIG. 4).

Figure 5A:
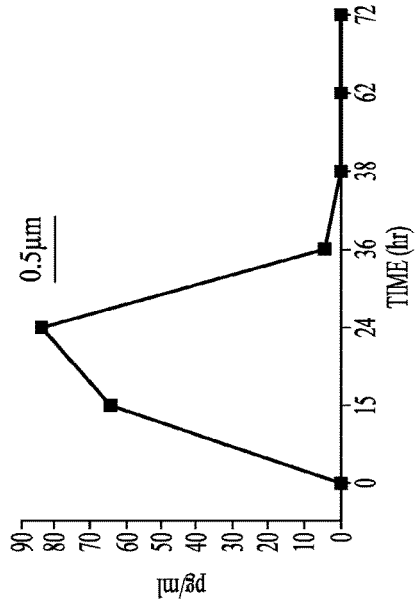
FIGS. 5A-5D shows the expression of MIP-1a in pg/ml by ELISA.
Figure 5B:
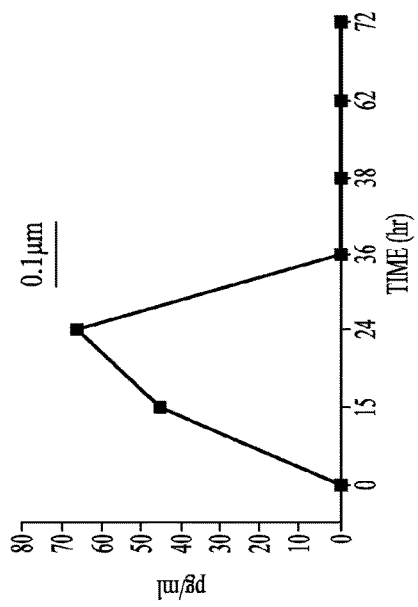
Figure 5C:
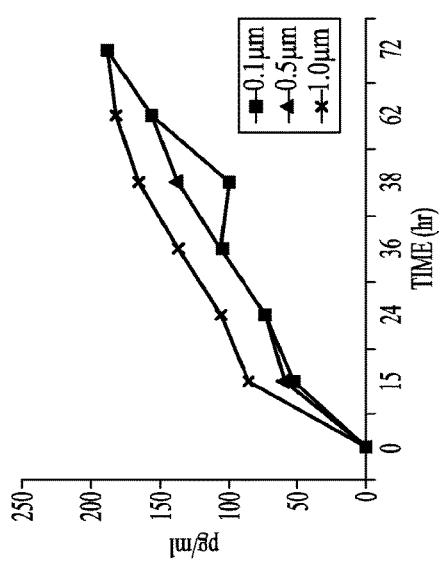
Figure 6A:
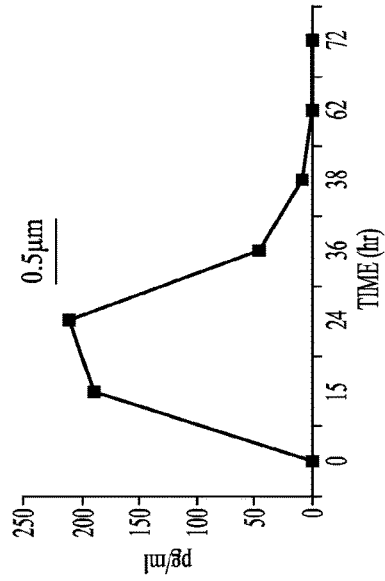
FIGS. 6A-6D shows the expression of MIP-3α in pg/ml by ELISA.
Figure 6C:
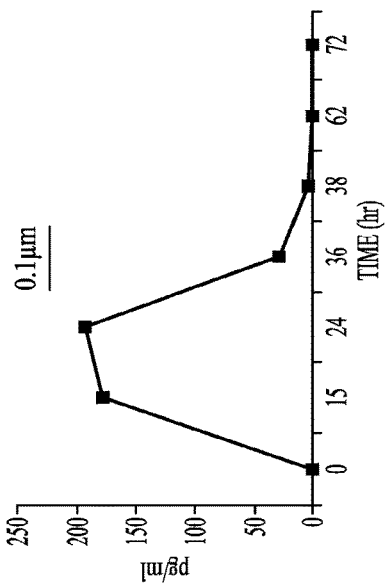
Figure 6B:
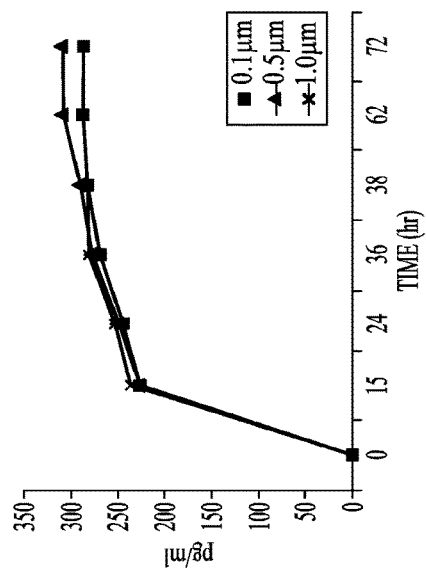

ELISA experiments were also performed to investigate the expression of MIP-1α (FIG. 5A-C) or MIP-3α (FIG. 6A-C) after the micro- and nano-particles were removed from the cells. MIP-1α or MIP-3α expression was assayed at time points ranging from 0 to 72 hours. Particles were removed after twelve hours. MIP-1α expression peaked at 24 hours and decreased to near undetectable levels after 36 hours (FIG. 5A-C). Particle size had little effect on the response or return to near undetectable levels (FIG. 5A-C). MIP-3α expression peaked at 24 hours when cells were incubated with particles 0.1 or 0.5 μmin size, and at 15 hours when cells were incubated with particles 1.0 μmin size (FIG. 6A-C). After 38 hours, expression of MIP-3u decreased to near undetectable levels regardless of particle size (FIG. 6A-C).

Figure 5D:
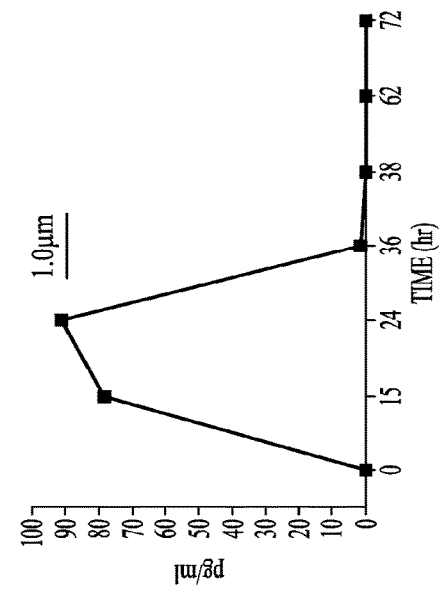
Figure 6D:
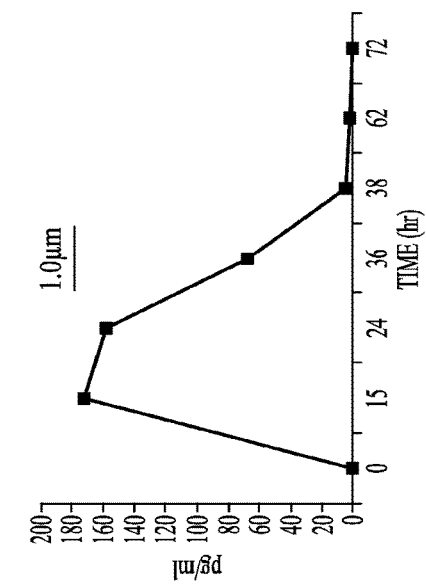

When cells were continuously incubated with micro- or nano-particles, the expression of MIP-1α steadily increased throughout the 72 hour measurement period (FIG. 5D). Expression of MIP-1α was slightly increased when particles were 1.0 μmin size in comparison to particles 0.1 or 0.5 μmin size (FIG. 5D). Expression of MIP-3α increased after 15 hours and increased only slightly for the remainder of the 72-measurement period (FIG. 6D).

Figure 9:
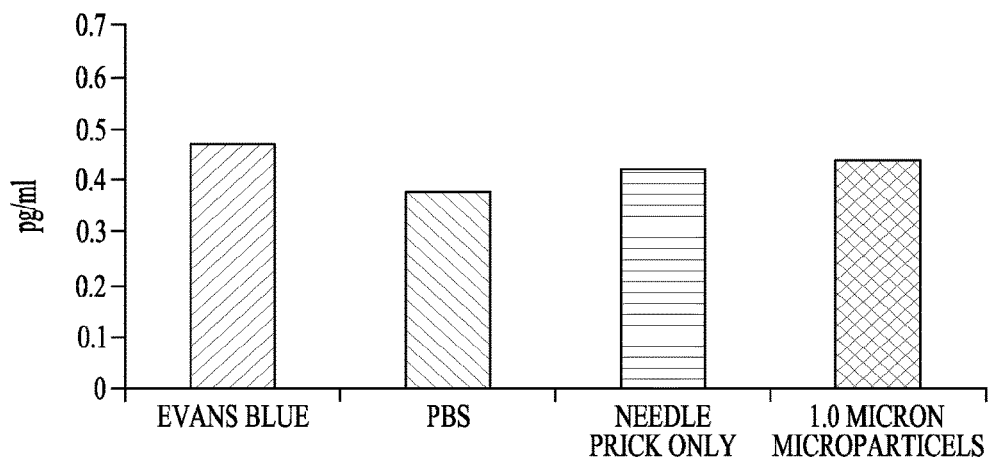
FIG. 9 shows expression of MIP-1α (pg/ml)in rat blood, where animals had been injected with 50 µl of evans blue, 50 µl of PBS, a needle prick only, or 50 µl of 1.0 µm particles suspended in PBS at a concentration of 25 mg/ml.
Figure 10:
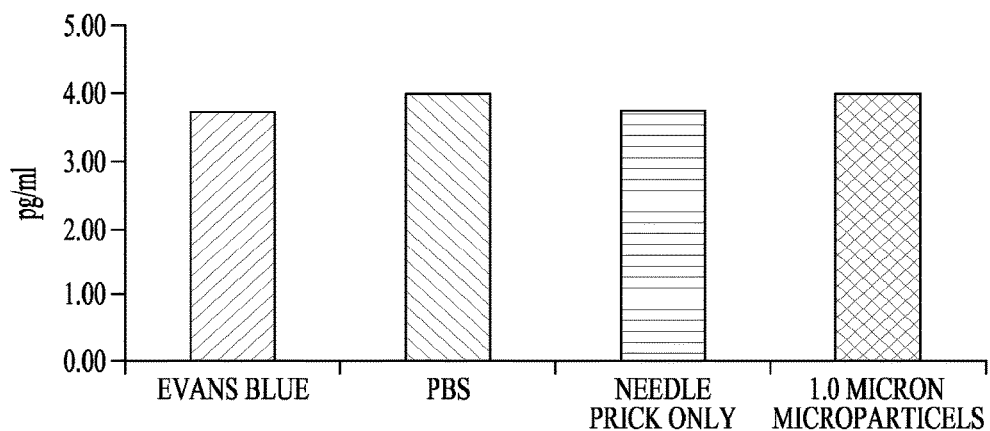
FIG. 10 shows expression of MIP-3α (pg/ml) in rat blood, where animals had been injected with evans blue, PBS, a needle prick only, or 50 µl of 1.0 µm particles suspended in PBS at a concentration of 25 mg/ml.

To further confirm that the phagocytosis of particles in the injection site resulted only in a localized inflammatory and not a systemic response, expression of MIP-1α (FIG. 9) and MIP-3α (FIG. 10), two markers of the classic immune response, were analyzed by ELISA from the circulating blood in treated and control rats. No significant changes in either marker from baseline levels were observed due to the injection of the particles in the quadriceps muscles clearly indicating that the immune response is localized to the site of injection and does not escalate to a systemic inflammatory response (FIGS. 9-10).

Metabolic bioanalysis: RAW 264.7 cells were incubated with micro- or nano-particles for 72 hours, or for 15 hours, after which the particles were removed and fresh particle-free medium was added every 12-15 hours (FIG. 7). Transiently exposed cells were cultured for a total of 24 hours, 48 hours, or 72 hours. Cells transiently exposed to particles were able to rapidly return to normal utilization of glucose and glutamine, and normal production of lactate following the removal of micro- or nano-particles (FIG. 7 A). Rapid clearance or degradation of the micro- or nano-spheres allow the cells to rapidly return to homeostasis once the particles are cleared or degraded. On the other hand, when cells were exposed to particles continuously for 72 hours, the use of glucose and glutamine was slowed in comparison to cells lacking particle exposure (FIG. 7B). This effect may be due to the redirection of the cell's resources for phagocytosis.

These results indicate that a localized and transitory immune response can be triggered that can be regulated to achieve a desired local immune response targeted to the removal of contaminating bacteria in the vicinity of the surgical implant without triggering a systemic inflammation response.

Additional Notes

The above description includes references to the incorporated drawings and examples. The examples and figures show, by way of illustration, specific embodiments in which the invention can be practiced. These embodiments are also referred to herein as "examples." Such examples can include elements in addition to those shown and described. However, the present inventors also contemplate examples in which only those elements shown and described are provided. Moreover, the present inventors also contemplate examples using any combination or permutation of those elements shown or described (or one or more aspects thereof), either with respect to a particular example (or one or more aspects thereof), or with respect-to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are openended, that is, a system, device, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The following statements of the invention are intended to describe possible elements or features of the invention according to the foregoing description given in the specification.

STATEMENTS DESCRIBING ASPECTS OF THE INVENTION

1. A method of reducing a microbial infection at a site in an animal in need thereof, comprising locally administering to the site an effective amount of a composition comprising particles having a diameter of about 1.0 nm to about 100 µm, to thereby reduce microbial infection at the site in the animal;
   wherein the particles inhibit bacteria from adhering to or colonizing the site, and
   wherein the composition is configured to biodegrade after activating macrophages without substantial activation of neutrophils.
2. The method of statement 1, wherein the composition coats or is administered with an implant or implantation device.
3. The method of statement 1 or 2, wherein the particles in the composition comprise an inorganic material, organic material, magnetic material, radioactive material, or a combination thereof.
4. The method of statement 3, wherein the inorganic material comprises metal, silica, alumina, titania, glass, ceramic, or a combination thereof.
5. The method of statement 4, wherein the glass comprises plain glass, precision glass, sieve calibration glass, high refraction index glass, hollow glass, dyed glass, or a combination thereof.
6. The method of statement 4, wherein the ceramic comprises zirconia or zirconium silicate.
7. The method of statement 3, wherein the organic material comprises polymethylmethacrylate, polystyrene, melamine, polylactide, or a combination thereof.
8. The method of statement 3, wherein the magnetic material also comprises silica, polystyrene, dextran, or a combination thereof.
9. The method of any of statements 1-8, wherein the particles further comprise a functional group.
10. The method of any of statements 1-9, wherein the particles further comprise a functional group selected from the group consisting of an amine, epoxy, carboxyl, avidin, streptavidin, protein A, fluorescent material, and a combination thereof.
11. The method of any of statements 1-10, wherein at least one of the particles is polystyrene.
12. The method of any of statements 1-11, wherein substantially all of the particles are adapted or configured for adhesion to bacteria; or wherein at least 70% of the particles are adapted or configured for adhesion to bacteria; or wherein at least 95% of the particles are adapted or configured for adhesion to bacteria.
13. The method of any of statements 1-12, wherein one or more particles has a diameter falling in the range of about 100 nm to about 0.5 µm; or wherein at least 70% of the particles have a diameter falling in the range of about 100 nm to about 0.5 µm.
14. The method of any of statements 1-13, wherein at least 70% of the particles have a shape that is substantially spherical, square, rectangular, planar, cuboidal, or a combination thereof.
15. The method of any of statements 1-14, wherein at least 70% of the particles are substantially smooth.
16. The method of any of statements 1-15, wherein at least 70% or at least 95% of the particles have an average surface roughness greater than 0.2 microns.
17. The method of any of statements 1-16, wherein the composition is embedded or impregnated into a surface of an implant.
18. The method of any of statements 1-17, wherein the composition is a coating on at least one surface of an implant.
19. The method of statement 17 or 18, wherein the implant comprises a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or any other implantable medical device.
20. The method of any of statements 17-19, wherein the implant is configured for implantation into bone.
21. The method of any of statements 17-19, wherein the implant is configured for implantation into a blood vessel.
22. The method of any of statements 17-19, wherein the implant is configured for implantation into a hernia, breast, bladder, anus, vagina, or penis.
23. The method of any of statements 1-22, wherein bacteria can adhere to the particles.
24. The method of any of statements 1-23, wherein the composition is a single layer coating on an implant.

25. The method of any of statements 1-24, wherein the composition is a multiple layer coating on an implant.

26. The method of any of statements 1-24, wherein the composition is a multiple layer coating on an implant and wherein one or more layers are configured to peel-off after administration.

27. The method statement 26, wherein the one or more layers peel-off over a time period of about 1 hour to about 1 week.

28. The method of statement 26 or 27, wherein the particle coating has 1 to 10 layers.

29. The method of any of statements 1-28, wherein the composition is a coating on at least one surface of an implant and wherein a particle is released from the coating over a time period of about 1 hour to about 1 week.

30. The method of statement 29, wherein the particles are released from the coating over a time period of about 72 hours.

31. The method of statement 29 or 30, wherein the particles are released from the coating over a time period of about 48 hours.

32. The method of any of statements 29-31, wherein the particles are released from the coating over a time period of about 24 hours.

33. The method of any of statements 29-32, wherein the particles are released from the coating over a time period of less than 24 hours.

34. The method of any of statements 1-33, wherein the composition further comprises an anti-bacterial agent, an anti-fungal agent, an anti-inflammatory agent, an chemotherapeutic agent, or a combination thereof.

35. The method of any of statements 1-34, wherein an anti-bacterial agent, an anti-fungal agent, an anti-inflammatory agent, an chemotherapeutic agent, or a combination thereof is released from the composition over time period of about 1 to about 72 hours.

36. The method of any of statements 1-34, wherein the composition comprises an antibacterial agent selected from the group consisting of β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, cefiriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol or any combination thereof.

37. The method of any of statements 1-36, wherein the composition comprises a concentration of an antibacterial agent ranging from about 0.01 mg per $cm^2$ to about 30 mg per $cm^2$ or greater.

38. The method of any of statements 1-37, wherein the composition comprises an antifungal agent selected from the group consisting of amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium. sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium. undecylenate, copper undecylenate, zinc undecylenate).

39. The method of any of statements 1-38, wherein the composition comprises a concentration of an antifungal agent ranging from about 0.01 mg per $cm^2$ to about 30 mg per $cm^2$ or greater.

40. The method of any of statements 1-39, wherein the composition comprises a chemotherapeutic agent selected from the group consisting of busulfan, hexamethylmelamine, thiotepa, cyclophosphamide, mechlorethamine, uramustine, melphalan, chlorambucil, carmustine, streptozocin, dacarbazine, temozolomide, cisplatin, carboplatin, ifosfamide, methotrexate, azathioprine, mercaptopurine, fludarabine, 5-fluorouracil, vincristine, vinblastine, vinorelbine, vindesine, paclitaxel, docetaxel, podophyllotoxin, irinotecan, topotecan, amsacrine, etoposide, etoposide phosphate, teniposide, dactinomycin, doxorubicin, daunorubicin, epirubicin, bleomycin, plicamycin, mitomycin, or a combination thereof.

41. The method of any of statements 1-40, wherein the composition comprises a concentration of a chemotherapeutic agent ranging from about 0.01 mg per $cm^2$ to about 30 mg per $cm^2$ or greater.

42. The method of any of statements 1-41, wherein the composition comprises one or more agents selected from the group consisting of a cytokine, a chemokine, an antibody, a peptide, a recombinant DNA, or a combination thereof.

43. The method of any of statements 1-42, wherein the composition further comprises a cytokine selected from the group consisting of IL-1, IL-2, IL-3, IL-4, IL-5, IL-6, IL-7, IL-8, IL-10, IL-12, IL-13, IL-15, IL-17, IL-18, IL-22, IL-23, IL-35, type I interferon, type II interferon, tumor necrosis factor-alpha, transforming growth factor-beta, granulocyte colony stimulating factor, granulocyte-monocyte colony stimulating factor, thymic stromal lymphopoietin, or a combination thereof.

44. The method of any of statements 1-43, wherein the composition further comprises a chemokine selected from the group consisting of CC chemokines, CXC chemokines, C chemokines, $CX_3C$ chemokines, or a combination thereof.

45. The method of any of statements 1-44, wherein the composition comprises a concentration of a chemokine ranging from about 0.01 mg per $cm^2$ to about 30 mg per $cm^2$ or greater.

46. The method of any of statements 1-45, wherein the method reduces bacterial titer at a site of an implant or implantation device.

47. An implant comprising:
one or more surfaces configured for implantation into an animal; and
a coating on the one or more surfaces, where the coating comprises a composition comprising particles with a diameter of about 1.0 nm to about 100 μm.

48. The implant of statement 47, wherein each particle comprises an inorganic material, organic material, magnetic material, radioactive material or a combination thereof.

49. The implant of statement 47 or 48, wherein the particles comprise an inorganic material selected from the group consisting of metal, silica, alumina, titania, glass, ceramic, and a combination thereof.

50. The implant of any of statements 47-49, wherein the particles comprise glass selected from the group consisting of plain glass, precision glass, sieve calibration glass, high refraction index glass, hollow glass, dyed glass, and a combination thereof.

51. The implant of statement 49, wherein the ceramic comprises zirconia or zirconium silicate.

52. The implant of statement 48, wherein the organic material is selected from the group consisting of polymethylmethacrylate, polystyrene, melamine, polylactide, and a combination thereof.

53. The implant of statement 48, wherein the magnetic material also comprises silica, polystyrene, dextran, or a combination thereof.

54. The implant of any of statements 47-53, further comprising a functional group selected from the group consisting of an amine, epoxy, carboxyl, avidin, streptavidin, protein A, fluorescent material, or a combination thereof.

55. The implant of any of statements 47-54, wherein at least 50% of the particles comprise polystyrene; or wherein at least 90% of the particles comprise polystyrene.

56. The implant of any of statements 47-55, wherein substantially all of the particles are adapted or configured for adhesion to bacteria; or wherein at least 70% of the particles are adapted or configured for adhesion to bacteria; or wherein at least 95% of the particles are adapted or configured for adhesion to bacteria.

57. The implant of any of statements 47-56, wherein one or more particles has a diameter falling in the range of about 100 nm to about 0.5 µm; or wherein at least 70% of the particles have a diameter falling in the range of about 100 nm to about 0.5 µm.

58. The implant of any of statements 47-57, wherein at least 70% of the particles have a shape that is substantially spherical, square, rectangular, planar, cuboidal, or a combination thereof.

59. The implant of any of statements 47-58, wherein at least 70% of the particles are substantially smooth.

60. The implant of any of statements 47-59 wherein at least 70% or at least 95% of the particles have an average surface roughness greater than 0.2 microns.

61. The implant of any of statements 47-60, wherein bacteria can adhere to the particles.

62. The implant of any of statements 47-61, wherein a coating is embedded or impregnated into one or more surfaces of the implant.

63. The implant of any of statements 47-62, wherein the coating comprises a single layer.

64. The implant of any of statements 47-63, wherein the coating comprises multiple layers.

65. The implant of any of statements 47-64, wherein the coating comprises multiple layers, and one or more of the layers are configured to peel-off after implantation of the implant.

66. The implant statement 65, wherein the one or more layers are configured to peel-off over a time period of about 1 hour to about 1 week.

67. The implant of any of statements 47-65, wherein the coating comprises about 1 to 10 layers.

68. The implant of any of statements 47-67, wherein the particles are released from the coating over a time period of about 1 hour to about 1 week.

69. The implant of any of statements 47-68, wherein the coating further comprises an anti-bacterial agent, an anti-fungal agent, an anti-inflammatory agent, an chemotherapeutic agent, or a combination thereof.

70. The implant of any of statements 47-69, wherein the coating further comprises an anti-bacterial agent, an anti-fungal agent, an anti-inflammatory agent, an chemotherapeutic agent, or a combination thereof that is released from the coating over time period of about 1 to about 72 hours.

71. The implant of any of statements 47-70, wherein the coating further comprises an antibacterial agent selected from the group consisting of β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, cefiriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol or any combination thereof.

72. The implant of any of statements 47-71, wherein the coating comprises an antibacterial agent concentration of about 0.01 mg per cm$^2$ to about 10 mg per cm$^2$.

73. The implant of any of statements 47-72, wherein the coating comprises an antifungal agent selected from the group consisting of amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate).

74. The implant of any of statements 47-73, wherein the coating comprises an antifungal agent concentration of about 0.01 mg per cm$^2$ to about 10 mg per cm$^2$.

75. The implant of any of statements 47-74, wherein the coating comprises a chemotherapeutic agent selected from the group consisting of busulfan, hexamethylmelamine, thiotepa, cyclophosphamide, mechlorethamine, uramustine, melphalan, chlorambucil, carmustine, streptozocin, dacarbazine, temozolomide, cisplatin, carboplatin, ifosfamide, methotrexate, azathioprine, mercaptopurine, fludarabine, 5-fluorouracil, vincristine, vinblastine, vinorelbine, vindesine, paclitaxel, docetaxel, podophyllotoxin, irinotecan, topotecan, amsacrine, etoposide, etoposide phosphate, teniposide, dactinomycin, doxorubicin, daunorubicin, epirubicin, bleomycin, plicamycin, mitomycin, or a combination thereof.

76. The implant of any of statements 47-75, wherein the coating further comprises one or more agents selected from the group consisting of a cytokine, a chemokine, an antibody, a peptide, a recombinant DNA, or a combination thereof.

77. The implant of any of statements 47-76, wherein the coating further comprises a cytokine selected from the group consisting of IL-1, IL-2, IL-3, IL-4, IL-5, IL-6, IL-7, IL-8, IL-10, IL-12, IL-13, IL-15, IL-17, IL-18, IL-22, IL-23, IL-35, type I interferon, type II interferon, tumor necrosis factor-alpha, transforming growth factor-beta, granulocyte colony stimulating factor, granulocyte-monocyte colony stimulating factor, thymic stromal lymphopoietin, or a combination thereof.

78. The implant of any of statements 47-77, wherein the coating further comprises a chemokine selected from the group consisting of CC chemokines, CXC chemokines, C chemokines, $CX_3C$ chemokines, or a combination thereof.

79. The implant of any of statements 47-78, wherein the implant comprises a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or a combination thereof.

80. The implant of any of statements 47-79, wherein the implant is configured for implantation into bone.

81. The implant of any of statements 47-80, wherein the implant is configured for implantation into a blood vessel.

82. The implant of any of statements 47-81, wherein the implant is configured for implantation into a hernia, breast, bladder, anus, vagina, or penis.

83. A method of manufacturing an implant or implantation device comprising coating the implant or the implantation device with a composition comprising particles having a diameter of about 1.0 nm to about 100 µm.

84. The method of statement 83, wherein the particles inhibit bacteria from adhering to or colonizing the site.

85. The method of statement 83 or 84, wherein the composition is configured to biodegrade after activating macrophages without substantial activation of neutrophils.

86. The method of any of statements 83-85, wherein the composition comprises an inorganic material, organic material, magnetic material, radioactive material, or a combination thereof.

87. The method of any of statements 83-86, wherein the composition comprises an inorganic material selected from the group consisting of metal, silica, alumina, titania, glass, ceramic, and a combination thereof.

88. The method of statement 83, wherein the glass is selected from the group consisting of plain glass, precision glass, sieve calibration glass, high refraction index glass, hollow glass, dyed glass, and a combination thereof.

89. The method of statement 87, wherein the ceramic further comprises zirconia or zirconium silicate.

90. The method of statement 86, wherein the organic material is selected from the group consisting of polymethylmethacrylate, polystyrene, melamine, polylactide, and a combination thereof.

91. The method of statement 86, wherein the magnetic material further comprises silica, polystyrene, dextran, or a combination thereof.

92. The method of any of statements 83-92, further comprising a functional group selected from the group consisting of amine, epoxy, carboxyl, avidin, streptavidin, protein A, fluorescent material, or a combination thereof.

93. The method of any of statements 83-92, wherein at least 500 of the particles comprise polystyrene; or wherein at least 90% of the particles comprise polystyrene.

94. The method of any of statements 83-93, wherein substantially all of the particles are adapted or configured for adhesion to bacteria; or wherein at least 70% of the particles are adapted or configured for adhesion to bacteria; or wherein at least 95% of the particles are adapted or configured for adhesion to bacteria.

95. The method of any of statements 83-91, wherein one or more particles has a diameter falling in the range of about 100 nm to about 0.5 µm; or wherein at least 70% of the particles have a diameter falling in the range of about 100 nm to about 0.5 µm.

96. The method of any of statements 83-95, wherein at least 700 of the particles have a shape that is substantially spherical, square, rectangular, planar, cuboidal, or a combination thereof.

97. The method of any of statements 83-96, wherein at least 70% of the particles are substantially smooth.

98. The method of any of statements 83-97, wherein at least 70% or at least 95% of the particles have an average surface roughness greater than 0.2 microns.

99. The method of any of statements 83-98, comprising embedding or impregnating the composition into a surface of an implant.

100. The method of any of statements 83-99, wherein the implant comprises a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or a combination thereof.

101. The method of any of statements 83-100, wherein the implant or the implantation device is configured for implantation into bone.

102. The method of any of statements 83-100, wherein the implant or the implantation device is configured for implantation into a blood vessel.

103. The method of any of statements 83-100, wherein the implant or the implantation device is configured for implantation into a hernia, breast, bladder, anus, vagina, or penis.

104. The method of any of statements 83-103, wherein bacteria can adhere to the particles.

105. The method of any of statements 83-104, comprising coating the implant or the implantation device with a single layer of the composition.

106. The method of any of statements 83-105, comprising coating the implant or the implantation device with multiple layers.

107. The method of any of statements 83-106 comprising coating the implant or the implantation device with multiple layers, wherein one or more layers are configured to peel-off after administration.

108. The method of statement 107, wherein the one or more layers peel-off over a time period of about 1 hour to about 1 week.

109. The method of any of statements 83-108, comprising coating the implant or the implantation device with 1 to 10 layers.

110. The method of any of statements 83-109, wherein composition is adapted or configured to release particles over a time period of about 1 hour to about 1 week.

111. The method of any of statements 83-110, wherein composition is adapted or configured to release particles over a time period of about 72 hours.

112. The method of any of statements 83-111, wherein composition is adapted or configured to release particles over a time period of about 48 hours.

113. The method of any of statements 83-112, wherein composition is adapted or configured to release particles over a time period of about 24 hours.

114. The method of any of statements 83-113, wherein the composition further comprises an anti-bacterial agent, an anti-fungal agent, an anti-inflammatory agent, an chemotherapeutic agent, or a combination thereof.

115. The method of any of statements 83-114, wherein the composition is adapted or configured to release an antibacterial agent, an anti-fungal agent, an anti-inflammatory agent, an chemotherapeutic agent, or a combination thereof over about 1 to about 72 hours.

116. The method of any of statements 83-115, wherein the composition further comprises an antibacterial agent selected from the group consisting of β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol or any combination thereof.

117. The method of any of statements 83-116, wherein the composition further comprises a concentration of an antibacterial agent ranging from about 0.01 mg per cm$^2$ to about 10 mg per cm$^2$.

118. The method of any of statements 83-117, wherein the composition further comprises an antifungal agent selected from the group consisting of amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate).

119. The method of any of statements 83-118, wherein the composition comprises a concentration of an antifungal agent ranging from about 0.01 mg per cm$^2$ to about 10 mg per cm$^2$.

120. The method of any of statements 83-119, wherein the composition comprises a chemotherapeutic agent selected from the group consisting of busulfan, hexamethylmelamine, thiotepa, cyclophosphamide, mechlorethamine, uramustine, melphalan, chlorambucil, carmustine, streptozocin, dacarbazine, temozolomide, cisplatin, carboplatin, ifosfamide, methotrexate, azathioprine, mercaptopurine, fludarabine, 5-fluorouracil, vincristine, vinblastine, vinorelbine, vindesine, paclitaxel, docetaxel, podophyllotoxin, irinotecan, topotecan, amsacrine, etoposide, etoposide phosphate, teniposide, dactinomycin, doxorubicin, daunorubicin, epirubicin, bleomycin, plicamycin, mitomycin, or a combination thereof.

121. The method of any of statements 83-120, wherein the composition comprises a concentration of a chemotherapeutic agent ranging from about 0.01 mg per cm$^2$ to about 10 mg per cm$^2$.

122. The method of any of statements 83-121, wherein the composition comprises one or more agents selected from the group consisting of a cytokine, a chemokine, an antibody, a peptide, a recombinant DNA, or a combination thereof.

123. The method of any of statements 83-122, wherein the composition further comprises a cytokine selected from the group consisting of IL-1, IL-2, IL-3, IL-4, IL-5, IL-6, IL-7, IL-8, IL-10, IL-12, IL-13, IL-15, IL-17, IL-18, IL-22, IL-23, IL-35, type I interferon, type II interferon, tumor necrosis factor-alpha, transforming growth factor-beta, granulocyte colony stimulating factor, granulocyte-monocyte colony stimulating factor, thymic stromal lymphopoietin, or a combination thereof.

124. The method of any of statements 83-123, wherein the composition further comprises a chemokine selected from the group consisting of CC chemokines, CXC chemokines, C chemokines, CX$_3$C chemokines, or a combination thereof.

125. The method of any of statements 83-124, wherein the composition comprises a concentration of a chemokine ranging from about 0.01 mg per cm$^2$ to about 10 mg per cm$^2$.

126. The method of any of statements 83-125, wherein the composition reduces bacterial titer at a site of an implant or implantation device.

127. The method of any of statements 83-126, wherein the composition reduces bacterial titer at a site of an implant or implantation device by at least 50%, or by at least 70%, or by at least 80%, or by at least 90%, or by at least 95%, or by at least 99%.

128. Use of a composition comprising particles with a diameter of about 1.0 nm to about 100 μm for reducing a microbial infection at a site in an animal.

129. The use of statement 128, wherein the particles inhibit bacteria from adhering to or colonizing the site.

130. The use of statement 128 or 129, wherein the composition is configured to biodegrade after activating macrophages without substantial activation of neutrophils.

131. The use of any of statements 128-130, wherein the composition coats or is administered with an implant or implantation device.

132. The use of any of statements 128-131, wherein the composition comprises inorganic material, organic material, magnetic material, radioactive material, or a combination thereof.

133. The use of statement 132, wherein the inorganic material comprises metal, silica, alumina, titania, glass, ceramic, or a combination thereof.

134. The use of statement 133, wherein the glass comprises plain glass, precision glass, sieve calibration glass, high refraction index glass, hollow glass, dyed glass, or a combination thereof.

135. The use of statement 134, wherein the ceramic further comprises zirconia or zirconium silicate.

136. The use of statement 132, wherein the organic material comprises polymethylmethacrylate, polystyrene, melamine, polylactide, or a combination thereof.

137. The use of statement 132, wherein the magnetic material further comprises silica, polystyrene, dextran, or a combination thereof.

138. The use of any of statements 128-137, further comprising a functional group selected from the group consisting of an amine, epoxy, carboxyl, avidin, streptavidin, protein A, fluorescent material, or a combination thereof.

139. The use of any of statements 128-138, wherein at least one of the particles is polystyrene.

140. The use of any of statements 128-139, wherein substantially all of the particles are adapted or configured for adhesion to bacteria; or wherein at least 70% of the particles are adapted or configured for adhesion to bacteria; or wherein at least 95% of the particles are adapted or configured for adhesion to bacteria.

141. The use of any of statements 128-140, wherein one or more particles has a diameter falling in the range of about 100 nm to about 0.5 µm; or wherein at least 70% of the particles have a diameter falling in the range of about 100 nm to about 0.5 µm.

142. The use of any of statements 128-141, wherein at least 70% of the particles have a shape that is substantially spherical, square, rectangular, planar, cuboidal, or a combination thereof.

143. The use of any of statements 128-142, wherein at least 70% of the particles are substantially smooth.

144. The use of any of statements 128-143, wherein at least 70% or at least 95% of the particles have an average surface roughness greater than 0.2 microns.

145. The use of any of statements 128-144, wherein the composition is embedded or impregnated into one or more surfaces of an implant or implantation device.

146. The use of statement 145, wherein the implant or implantation device comprises a sponge, bandage, suture, catheter, stent, pin, staple, mesh, valve, pacemaker, conduit, cannula, appliance, scaffold, contraceptive device, central line, pessary, tube, drain, trochar, plug, cerebrospinal fluid drain, tracheostomy, endotracheal tube, chest tube, rod, screw, orthopedic appliance, bandage, suture or any other implantable medical device.

147. The use of statement 145 or 146, wherein the implant or implantation device is configured for implantation into bone.

148. The use of statement 145 or 146, wherein the implant or implantation device is configured for implantation into a blood vessel.

149. The use of statement 145 or 146, wherein the implant is configured for implantation into a hernia, breast, bladder, anus, vagina, or penis.

150. The use of any of statements 128-149, wherein bacteria can adhere to the particles.

151. The use of any of statements 128-150, wherein the composition is coated onto an implant or implantation device in a single layer.

152. The use of any of statements 128-151, wherein the composition is coated onto an implant or implantation device in multiple layers.

153. The use of any of statements 128-152, wherein the composition is coated onto an implant or implantation device in multiple layers, and wherein one or more layers are configured to peel-off after administration.

154. The use of any of statements 128-153, wherein the composition is coated onto an implant or implantation device in multiple layers, and wherein the one or more layers peel-off over a time period of about 1 hour to about 1 week.

155. The use of any of statements 128-154, wherein the composition is coated onto an implant or implantation device in 1 to 10 layers.

156. The use of any of statements 128-155, wherein a particle is released from the composition over a time period of about 1 hour to about 1 week.

157. The use of any of statements 128-156, wherein the particles are released from the composition over a time period of about 72 hours.

158. The use of any of statements 128-157, wherein the particles are released from the composition over a time period of about 48 hours.

159. The use of any of statements 128-158, wherein the particles are released from the composition over a time period of about 24 hours.

160. The use of any of statements 128-159, wherein the particles are released from the composition over a time period of less than 24 hours.

161. The use of any of statements 128-160, wherein the composition further comprises an anti-bacterial agent, an anti-fungal agent, an anti-inflammatory agent, an chemotherapeutic agent, or a combination thereof.

162. The use of any of statements 128-161, wherein the composition further comprises an anti-bacterial agent, an anti-fungal agent, an anti-inflammatory agent, a chemotherapeutic agent, or a combination thereof is released from the coating over time period of about 1 to about 72 hours.

163. The use of any of statements 128-162, wherein the composition comprises an antibacterial agent selected from the group consisting of β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoximie, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol or any combination thereof.

164. The use of any of statements 128-163, wherein the composition comprises a concentration of an antibacterial agent ranging from about 0.01 mg per $cm^2$ to about 10 mg per $cm^2$.

165. The use of any of statements 128-164, wherein the composition comprises an antifungal agent selected from the group consisting of amphotericin B, flucytosine, fluconazole, griseofulvin, miconazole nitrate, terbinafine hydrochloride, ketoconazole, itraconazole, undecylenic acid and chloroxylenol, ciclopirox, clotrimazole, butenafine hydrochloride, nystatin, naftifine hydrochloride, oxiconazole nitrate, selenium sulfide, econazole nitrate, terconazole, butoconazole nitrate, carbol-fuchsin, clioquinol, methylrosaniline chloride, sodium thiosulfate, sulconazole nitrate, terbinafine hydrochloride, tioconazole, tolnaftate, undecylenic acid and undecylenate salts (calcium undecylenate, copper undecylenate, zinc undecylenate).

166. The use of any of statements 128-165, wherein the composition comprises a concentration of an antifungal agent ranging from about 0.01 mg per $cm^2$ to about 10 mg per $cm^2$.

167. The use of any of statements 128-166, wherein the composition comprises a chemotherapeutic agent selected from the group consisting of busulfan, hexamethylmelamine, thiotepa, cyclophosphamide, mechlorethamine, uramustine, melphalan, chlorambucil, carmustine, streptozocin, dacarbazine, temozolomide, cisplatin, carboplatin, ifosfamide, methotrexate, azathioprine, mercaptopurine, fludarabine, 5-fluorouracil, vincristine, vinblastine, vinorelbine, vindesine, paclitaxel, docetaxel, podophyllotoxin, irinotecan, topotecan, amsacrine, etoposide, etoposide phosphate, teniposide, dactinomycin, doxorubicin, daunorubicin, epirubicin, bleomycin, plicamycin, mitomycin, or a combination thereof.

168. The use of any of statements 128-167, wherein the composition comprises a concentration of a chemotherapeutic agent ranging from about 0.01 mg 10 per $cm^2$ to about 10 mg per $cm^2$.

169. The use of any of statements 128-168, wherein the composition comprises one or more agents selected from the group consisting of a cytokine, a chemokine, an antibody, a peptide, a recombinant DNA, or a combination thereof.

170. The use of any of statements 128-169, wherein the composition further comprises a cytokine selected from the group consisting of IL-1, IL-2, IL-3, IL-4, IL-5, IL-6, IL-7, IL-8, IL-10, IL-12, IL-13, IL-15, IL-17, IL-18, IL-22, IL-23, IL-35, type I interferon, type II interferon, tumor necrosis factor-alpha, transforming growth factor-beta, granulocyte colony stimulating factor, granulocyte-monocyte colony stimulating factor, thymic stromal lymphopoietin, or a combination thereof.

171. The use of any of statements 128-170, wherein the composition further comprises a chemokine selected from the group consisting of CC chemokines, CXC chemokines, C chemokines, $CX_3C$ chemokines, or a combination thereof.

172. The use of any of statements 128-171, wherein the composition comprises a concentration of a chemokine ranging from about 0.01 mg per $cm^2$ to about 10 mg per $cm^2$.

173. The use of any of statements 128-172, wherein the use reduces bacterial titer at a site of an implant or implantation device.

What is claimed:

1. A method of reducing a microbial infection at a surgical site, wound site, site of infection, or injection site in an animal in need thereof, comprising:
    locally administering to the site an effective amount of a collection of discrete particles that are biodegradable, each particle having a diameter of about 1.0 nm to about 100 µm, wherein each of the particles comprises
    (A) polylactide, Poly(glycolic acid) (PGA), Poly(lactic acid) (PLA), Poly (Lactide-co-Glycolide) copolymer (PLGA), poly(D,L-glycolide) (PGA), poly(glycerol sebacate) (PGSA), Poly(ε-caprolactone), polyhydroxybutyrate (PHB), polyhydroxyvalerate (PHV), polydioxanone (PDS), poly(pyranose), poly(furanose), polyanhydride, polyorthoester, poly(hydroxyl acid), poly (lactone), poly (amino acid), poly(anhydride), poly (methane), poly (orthoester), poly (phosphazine), poly (phosphoester), poly (lactic co-glycolic) acid, poly (ether ester)s, synthetic poly(amino acids), polycarbonates, poly(hydroxyalkanoate)s, poly(caprolactone)s, poly(cyanoacrylate), poly(alkyl cyanoacrylate), poly(ketal), poly(caprolactone), poly(acetal), poly(hydroxy-ester), poly(hydroxyl-alkanoate), poly (propylene-fumarate), poly(ester), poly(ethers), poly (carbonates), poly(amide), poly(siloxane), poly(silane), poly(sulfide), poly(imides), poly(urea), poly(amide-enamine), poly(organic acid), poly(electrolytes), poly (p-dioxanone), poly(olefin), poloxamer, polyurethane, or a combination thereof; and
    (B) zein, modified zein, casein, gelatin, gluten, serum, albumin, collagen, actin, a-fetoprotein, globulin, macroglobulin, cohesin, laminin, fibronectin, fibrinogen, osteocalcin, osteopontin, osteoprotegerin, cyclic sugars, cyclodextrins, synthetic derivatives of cyclodextrins, glycolipids, glycosaminoglycans, oligosaccharides, alginate, carageenan, celluloses, chondroitin sulfate, curdlan, dextrans, elsinan, fuicellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, poly(3-hydoxyalkanoates), poly(3-hydroxy fatty acids), or a combination thereof,
    wherein at least 70% of the particles are configured to prevent bacterial adhesion and biofilm formation at the site,
    wherein at least 70% of the particles have an average surface roughness greater than 0.2 microns, and
    wherein the particles do not comprise a therapeutic agent.

2. The method of claim 1, wherein at least 70% of the particles have a diameter between 100 nm and 0.5 µm.

3. The method of claim 1, wherein at least 70% of the particles have a shape that is selected from the group consisting of substantially smooth, spherical, square, rectangular, planar, cuboidal, and combinations thereof.

4. The method of claim 1, wherein the collection of discrete particles comprises one or more layers that coat an implantable device, and wherein one or more layers are configured to peel-off over a time period between 1 hour and 1 week after the implantable device is administered.

5. The method of claim 1, wherein administering the collection of discrete particles reduces bacterial titer at the site by at least 50%.

6. The method of claim 1, wherein the collection of discrete particles coats at least a portion of the site.

7. The method of claim 1, wherein the particles are not part of a film.

8. The method of claim 1, wherein the collection of discrete particles is administered to the site with a carrier.

9. The method of claim 8, wherein the collection of discrete particles is administered to the site in a suspension.

10. The method of claim 1, wherein the particles are polylactide particles.

11. The method of claim 10, wherein the polylactide particles have an average diameter between 0.5 µm and 3.0 µm.

* * * * *